United States Patent
Busse et al.

(10) Patent No.: US 10,835,500 B2
(45) Date of Patent: Nov. 17, 2020

(54) MEDICAMENT FOR ACCELERATED WOUND HEALING

(71) Applicant: Symrise AG, Holzminden (DE)

(72) Inventors: Daniela Busse, Dortmund (DE); Heike Conrad, Göttingen (DE); Hanns Hatt, Bochum (DE)

(73) Assignee: Symrise AG, Holzminden (DE)

( * ) Notice: Subject to any disclaimer, the term of this patent is extended or adjusted under 35 U.S.C. 154(b) by 270 days.

(21) Appl. No.: 15/310,195

(22) PCT Filed: Jun. 16, 2015

(86) PCT No.: PCT/EP2015/063386
§ 371 (c)(1),
(2) Date: Nov. 10, 2016

(87) PCT Pub. No.: WO2015/193262
PCT Pub. Date: Dec. 23, 2015

(65) Prior Publication Data
US 2017/0258739 A1    Sep. 14, 2017

(30) Foreign Application Priority Data
Jun. 19, 2014 (EP) .................... 14173155

(51) Int. Cl.
*A61K 31/045* (2006.01)
*A61K 9/00* (2006.01)

(52) U.S. Cl.
CPC .......... *A61K 31/045* (2013.01); *A61K 9/0014* (2013.01)

(58) Field of Classification Search
CPC ........................... A61K 31/045; A61K 9/0014
See application file for complete search history.

(56) References Cited

U.S. PATENT DOCUMENTS 5,759,556 A * 6/1998 Burger ................. A61K 8/34
424/401

FOREIGN PATENT DOCUMENTS

WO  2008/068683 A1  6/2008
WO  2009/153572 A1  12/2009

OTHER PUBLICATIONS

Elson (Journal of the American Academy of Dermatology; vol. 39, No. 2, Part 3; 1998; S79-S81).*

* cited by examiner

*Primary Examiner* — Pancham Bakshi
(74) *Attorney, Agent, or Firm* — Dilworth & Barrese, LLP

(57) ABSTRACT

A medicament for accelerated wound healing is proposed containing derivatives of the formula (I), in which $R^1$ stands for hydrogen or methyl.

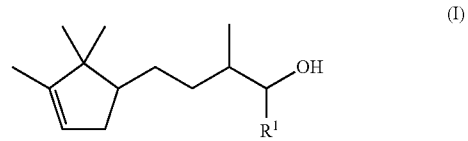

(I)

7 Claims, 12 Drawing Sheets

Figure 1:
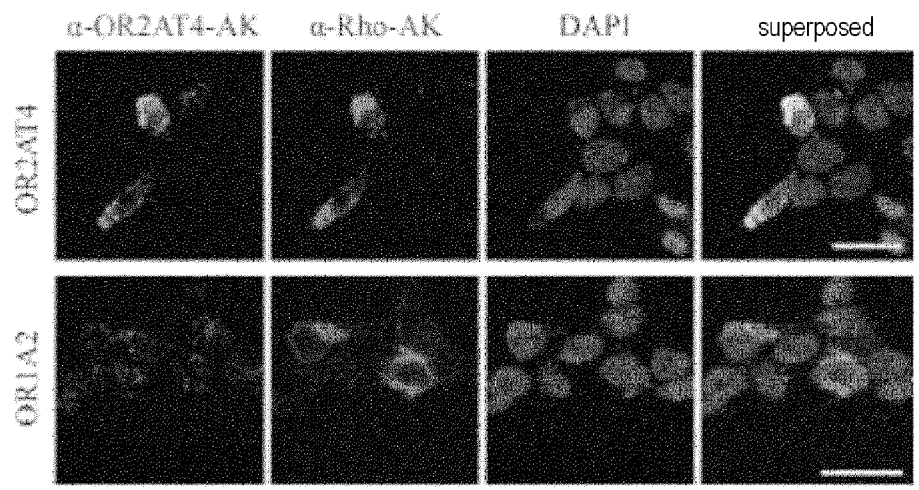

Heterologous expression of OR2AT4 in Hana3A cells

Membrane expression of OR2AT4 in Hana3A cells

Determination of receptive field of recombinantly expressed OR2AT4

Antagonists of recombinantly expressed OR2AT4

Receptive field of OR2AT4 and structural formulae of the odorants investigated

Expression of OR2AT4 in various human cell types and tissues

Expression of OR2AT4 in HaCaT cells and human primary keratinocytes

Expression of OR2AT4 in human skin sections

Effect of OR2AT4 ligand Sandalore on intracellular calcium concentration of cultivated keratinocytes Effect of gap junction blockers on sensitization of Sandalore-induced calcium signals Pharmacological characterization of Sandalore-induced signal cascade in human keratinocytes Expression analysis of signal cascade components and structurally related proteins by means of NGS data and RT-PCR Expression analyses of AC3 and CNGA1 by means of immunocytochemical stains RNA interference experiments for verifying the participation of OR2AT4 in Sandalore-induced calcium signals in HaCaT cells Action of antagonists of OR2AT4 on Sandalore-induced calcium signals in HaCaT cells Action of Sandalore long-term stimulation on morphology, growth, and migration processes in keratinocytes Action of Sandalore stimulation on the phosphorylation of MAP kinases in skin cells Action of Sandalore stimulation on human keratinocytes in an *in vivo* "wound healing" assay Investigation of interleukin secretion and phosphorylation of Akt protein kinase after Sandalore stimulation

MEDICAMENT FOR ACCELERATED WOUND HEALING

FIELD OF THE INVENTION

The invention concerns the field of pharmacy, and relates to drugs specially for the acceleration of wound healing that contain special compounds with a sandalwood odor.

PRIOR ART

Wound healing refers to the body's endogenous process of closing a wound by restoring the damaged body tissue to the greatest possible extent. This is a natural biological process that begins only minutes after occurrence of the would, as has been established by enzyme histochemical methods. The platelets are sent to the damaged site and attempt to close it. In some cases, scab formation occurs by exudation (secretion of fluid), which also causes the itching frequently accompanying wound healing.

Wound healing can be divided into various phases. Initially, after the destroyed blood vessel is closed by a clot, there are no further macroscopically or microscopically visible reactions. This first latency phase leads into an exudation phase, in which foreign bodies and bacteria are washed from the wound by wound secretion exuding from the wound. In this phase, the cells and hormones of the immune system play an essential role, not only in killing bacteria or viruses that have invaded the wound, but also in stimulating the healing process itself. In clot formation, a fibrin network is formed that acts as an adhesive to close adjacent margins of the wound. Clear wound secretion composed of serum is permeated with inflammatory cells. In the course of this phase, mitosis in the wound area increases. In the wound area, monocytes mature into macrophages that clear away cell debris and plugs. Fibroblasts, which develop from connective tissue cells that have infiltrated the wound, but are also present in the wound margin and reproduce by cell division, carry out the actual reconstruction work in the following phase.

In the following granulation phase, the wound defect is increasingly filled by proliferation of new connective tissue. Simultaneously with cell-rich filling of a wound defect, the fibrin network is broken down (fibrinolysis) by plasmin. Vascularization, i.e. an increase in the number of blood vessels, takes place by capillary growth. The fibroblasts produce hexosamine-containing acidic mucopolysaccharides, which function as an extracellular base substance of the connective tissue and, via intracellular preliminary stages, form the final extracellular collagen connective tissue fibers. The process over time is highly complex and is subject to the influence of numerous growth factors (cytokines).

Finally, in the regeneration phase, the wound is closed at the surface by epithelialization. One-third of the diameter of a well-granulating wound closes exclusively by contraction, and the other two-thirds close due to neoformation or cell division of epithelial cells and migration via fibrin from the wound margin to the center of the wound. The underlying granulation tissue increasingly forms collagen fibers, after which restoration of all skin layers is virtually complete. The further increase in the strength of the scar tissue depends on moistening, solidifying, and orientation of the collagen fibers. The water content of the tissue decreases, and the scar, which initially protruded slightly above skin level, normally contracts to below skin level. The vascularity of the scar tissue also decreases. The originally fresh red scar turns white.

Numerous pharmaceutically active ingredients that support wound healing are known from the prior art. Examples include aminothiazoles (EP 0967980 B1), arylsulfoaminopyran carboxylic acid hydroxymides (EP 1070058 B1), cyanoanthranilamides (EP 1387838 B1), antichymotrypsin polypeptides (EP 1392354 B1), and dipyridyl dihydropyrazoles (EP 1877396 B1). The mechanisms of action of these substances are completely different: the spectrum ranges from secretion of growth factors or special interleukins and inhibition of HIF prolyl 4-hydroxylase to the preparation of integrin receptor antagonists.

Reference is also made to the following documents:

Skin care agents comprising 0.001-10% retinol, 0.0001-50% of an aliphatic cyclic unsaturated compound (such as Brahmanol), and a cosmetically acceptable carrier are the subject matter of U.S. Pat. No. 5,759,556 A (Chesebrough). These preparations are used in the treatment of psoriasis.

WO 2008/068683 A1 (Firmenich) relates to a flavoring composition comprising an antimicrobial key component, and optionally at least one commonly-used flavoring component (such as Sandalore or Brahmanol), wherein the antimicrobial key components include 3,4-dimethylphenol together with one or a plurality of antimicrobial flavoring components, each of which has a minimum inhibitory concentration of 1000 ppm or less against two or more strains selected from *Fusobacterium nucleatum, Fusobacterium sp., Porphyromonas gingivalis, Prevotella intermedia, Klebsiella pneumoniae, Veillonella alcalescens, Bacteroides melaninogenicus/forsythus, Selenomonas sputagena, Porphyromonas endodontalis, Prevotella melaninogenica*, and *Streptococcus mutans*. These preparations are used to treat parodontitis.

The use of a sandalwood extract or a sandalwood analog (such as Sandalore) as an additive in animal feed to reduce the growth of pathogenic bacteria in the digestive system of ruminants and horses is known from WO 2009/153572 A1 (Aberystwith Univ.).

Sandalwood oil has long been one of the natural substances thought to support wound healing. This essential oil, which is obtained from the wood of the tropical sandal tree by steam distillation, contains numerous species whose detailed action remains unknown to this day. In particular, it is not known which components are responsible for the anti-inflammatory properties. Here, it should be noted that because of its extensive use as a raw material for perfume, natural sandalwood oil has become a rate and highly expensive feed stock.

Consequently, the object of the invention was to identify the anti-inflammatory components of sandalwood oil, in order in this manner to provide drugs for the acceleration of wound healing that in particular also support wound healing and above all stimulate cell proliferation and the expression and secretion of interleukin IL-1α. Identification of the active species should at the same time pave the way for synthesizing these substances in order to protect natural resources and contribute toward preserving biodiversity.

DESCRIPTION OF THE INVENTION

The invention relates to a drug containing derivatives of the formula (I),

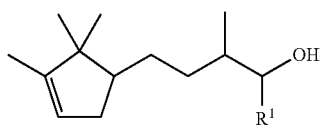

(I)

in which R1 denotes hydrogen or methyl, for acceleration of wound healing.

The derivatives of the formula (I) are preferably odorants with a sandalwood odor such as Sandalore® (R1=methyl) or Brahmanol® (R1=hydrogen). Both substances are freely available on the market and have so far only been used as odorants with a sandalwood odor.

Surprisingly, none of the known components of sandalwood oil has be found to be anti-inflammatory or to accelerate wound healing under test conditions. Instead, the two synthetic substances Sandalore and Brahmanol, which are closely structurally related to the components of sandalwood oil and also have a sandalwood-like odor, have been identified as the only antagonists of the olfactory receptor OR2AT4, which is found in the skin, among other tissues, and are the only agonists that can activate this receptor. In calcium imaging experiments, 80 to 90% of a sample of HaCaT cells and primary keratinocytes was repeatedly stimulated by these two substances, with calcium signals showing significant sensitization, i.e. an increase in signal amplitude after each additional application.

Activation of the receptor and triggering of the signal cascade were accompanied by an increase in the proliferation and migration of the HaCaT cells. This showed that the two substances stimulated phosphorylation of the MAP kinases p38 and ERK1/2, which are involved in epidermal wound healing. It was shown in an in vitro wound scratch assay that scratches closed 26% more quickly in HaCaT cells and 34% more quickly in keratinocytes when the cells were treated with 500 µM of Sandalore or Brahmanol.

Finally, the results confirm that by means of the two synthetic sandalwood odorants, the expression and secretion of IL-1α are increased, and the protein kinase Akt, which is involved in differentiation processes of human keratinocytes, is activated.

This finding is all the more surprising in that the two synthetic substances, which do not constitute components of sandalwood oil, are only intended per se to be tested for reference purposes.

However, it can now be definitely concluded based the present results that the administration of Sandalore® and/or Brahmanol®, preferably by topical application to the skin, causes acceleration of wound healing, primarily by activation of the receptor OR2AT4 and the cell proliferation and migration caused thereby following stimulation of phosphorylation of MAP kinases, and by increased IL-1α secretion.

Drugs

The drugs according to the invention are ordinarily topically applied. They may be used, for example, in the form of lotions, creams, emulsions, gels, ointments, or sprays. It is also possible to impregnate or coat corresponding dressing materials, such as patches, with these preparations.

The concentration of the active ingredients relative to the final drug formulation (i.e. active ingredient plus pharmaceutically reliable carrier, and optionally additives) can be approx. 0.001 to approx. 2 wt. %, preferably approx. 0.01 to approx. 1 wt. %, and particularly preferably approx. 0.1 to approx. 0.5 wt. %.

The drugs can further contain typical auxiliaries and additives, such as mild surfactants, oil components, emulsifiers, pearlescent waxes, bodying agents, thickeners, superfatting agents, stabilizers, polymers, silicone compounds, fats, waxes, lecithins, phospholipids, UV protective factors, emollients, biogenic active ingredients, antioxidants, hydrotropes, solubilizers, preservatives, perfume oils, dyes, and the like.

Surfactants

As surface-active substances, anionic, nonionic, cationic and/or amphoteric or zwitterionic surfactants whose content of the agents is ordinarily approximately 1 to 70, preferably 5 to 50, and in particular 10 to 30 wt % may be included. Typical examples of anionic surfactants are soaps, alkyl benzene sulfonates, alkane sulfonates, olefin sulfonates, alkyl ether sulfonates, glycerol ether sulfonates, α-methyl ester sulfonates, sulfofatty acids, alkyl sulfates, alkyl ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and the salts thereof, fatty acid isethionates, fatty acid sarcosinates, fatty acid taurides, N-acylamino acids such as acyl lactylates, acyl tartrates, acyl glutamates, and acyl aspartates, alkyl oligoglucoside sulfates, protein fatty acid condensation products (in particular wheat-based plant products) and alkyl (ether) phosphates. If the anionic surfactants contain polyglycol ether chains, these may exhibit a conventional, but preferably a narrowed homolog distribution. Typical examples of nonionic surfactants are fatty alcohol polyglycol ethers, alkyl phenol polyglycol ethers, fatty acid polyglycol esters, fatty acid amide polyglycol ethers, fatty amine polyglycol ethers, alkoxylated triglycerides, mixed ethers or mixed formulas, optionally partially oxidized alk(en)yl oligoglycosides or glucuronic acid derivatives, fatty acid N-alkyl glucamides, protein hydrolysates (in particular wheat-based plant products), polyol fatty acid esters, sugar esters, sorbitan esters, polysorbates and amine oxides. If the nonionic surfactants contain polyglycol ether chains, these may exhibit a conventional, but preferably a narrowed homolog distribution. Typical examples of cationic surfactants are quaternary ammonium compounds such as dimethyl distearylammonium chloride, and esterquats, in particular quaternized fatty acid trialkanolamine ester salts. Typical examples of amphoteric or zwitterionic surfactants are alkyl betaines, alkylamidobetaines, aminopropionates, aminoglycinates, imidazolinium betaines and sulfobetaines. The above-mentioned surfactants are exclusively known compounds. Typical examples of particularly suitable mild surfactants, i.e. particularly gentle to the skin, are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkyl amidobetaines, amphoacetals and/or protein fatty acid condensates, the latter preferably based on wheat proteins.

Oil Components

Examples of suitable oil components include Guerbet alcohols based on fatty alcohols with 6 to 18, and preferably 8 to 10 carbon atoms, esters of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$ fatty acids with branched alcohols, in particular 2-ethyl hexanol, esters of $C_{18}$-$C_{38}$ alkyl hydroxycarboxylic acids with linear or branched $C_6$-$C_{22}$ fatty alcohols, in particular dioctyl malate, esters of linear and/or branched fatty acids with multivalent alcohols (such as propylene glycol, dimer diol or trimer triol) and/or Guerbet alcohols, triglycerides based on $C_6$-$C_{10}$ fatty acids, liquid mono/di/triglyceride mixtures based on $C_6$-$C_{18}$ fatty acids, esters of $C_6$-$C_{22}$ fatty alcohols and/or Guerbet alcohols with aromatic carboxylic acids, in particular benzoic acid, esters of $C_2$-$C_{12}$ dicarboxylic acids with linear or branched alcohols with 1 to 22 carbon atoms or polyols with 2 to 10 carbon atoms and 2 to 6 hydroxyl groups, vegetable oils, branched primary alcohols, substituted cyclohexanes, linear and branched $C_6$-$C_{22}$ fatty alcohol carbonates such as dicaprylyl carbonate (Cetiol® CC), Guerbet carbonates based on fatty alcohols with 6 to 18, and preferably 8 to 10 carbon atoms, esters of benzoic acid with linear and/or branched $C_6$-$C_{22}$ alcohols (e.g. Finsolv® TN), linear or branched, symmetrical or asymmetrical dialkyl ethers with 6 to 22 carbon atoms per alkyl group such as dicaprylyl ether (Cetiol® OE), ring-opening products of epoxidized fatty acid esters with polyols, silicone oils (cyclomethicones, silicone methicone types, etc.) and/or aliphatic or naphthenic hydrocarbons such as squalane, squalene, or dialkyl cyclohexane.

Emulsifiers

Emulsifiers which may be used are for example nonionogenic surfactants from at least one of the following groups:
  addition products of 2 to 30 mol of ethylene oxide and/or 0 to 5 mol of propylene oxide onto linear fatty alcohols with 8 to 22 carbon atoms, fatty acids with 12 to 22 carbon atoms, alkyl phenols with 8 to 15 carbon atoms in the alkyl group, as well as alkylamine with 8 to 22 carbon atoms in the alkyl radical;
  alkyl and/or alkenyl oligoglycosides with 8 to 22 carbon atoms in the alk(en)yl radical and ethoxylated analogs thereof;
  addition products of 1 to 15 mol of ethylene oxide onto castor oil and/or hardened castor oil;
  addition products of 15 to 60 mol of ethylene oxide onto castor oil and/or hardened castor oil;
  partial esters of glycerol and/or sorbitan with unsaturated, linear or saturated, branched fatty acids with 12 to 22 carbon atoms and/or hydroxycarboxylic acids with 3 to 18 carbon atoms as well as adducts thereof with 1 to 30 mol of ethylene oxide;
  partial esters of polyglycerol (average intrinsic degree of condensation 2 to 8), polyethylene glycol (molecular weight 400 to 5000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids with 12 to 22 carbon atoms and/or hydroxycarboxylic acids with 3 to 18 carbon atoms, as well as adducts thereof with 1 to 30 mol of ethylene oxide;
  mixed esters of pentaerythritol, fatty acids, citric acid and fatty alcohol and/or mixed esters of fatty acids with 6 to 22 carbon atoms, methyl glucose and polyols, preferably glycerol or polyglycerol;
  mono-, di- and trialkyl phosphates as well as mono-, di- and/or tri-PEG alkyl phosphates and salts thereof;
  wool wax alcohols;
  polysiloxane/polyalkyl/polyethers copolymers or corresponding derivatives;
  block copolymers, e.g. polyethylene glycol-30 dipolyhydroxystearate;
  polymer emulsifiers, e.g. Pemulen grades (TR-1,TR-2) from Goodrich or Cosmedia® SP from Cognis;
  polyalkylene glycols, and
  glycerol carbonate.

In the following, particularly suitable emulsifiers are discussed in further detail:

Alkoxylates. The addition products of ethylene oxide and/or propylene oxide onto fatty alcohols, fatty acids, alkyl phenols or castor oil are known, commercially available products. These are homologous mixtures whose average degree of alkoxylation corresponds to the ratio of the amounts ethylene oxide and/or propylene oxide and substrates with which the addition reaction is carried out. $C_{12/18}$ fatty acid mono- and diesters of addition products of ethylene oxide to glycerol are known as refatting agents for cosmetic preparations.

Alkyl and/or alkenyl oligoglycosides. Alkyl and/or alkenyl oligoglycosides, their production, and their use are known from prior art. They are produced in particular by reacting glucose or oligosaccharides with primary alcohols with 8 to 18 carbon atoms. With respect to the glycoside radical, both monoglycosides, in which a cyclic sugar radical is glycosidically boned to the fatty alcohol, and oligomeric glycosides with a preferred degree of oligomerization of approximately 8 are suitable. Here, the degree of oligomerization is a statistical average value upon which a homolog distribution common for such technical products is based.

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride, as well as technical mixtures thereof, which can contain minor subordinate amounts of triglycerides from the production process. Addition products of 1 to 30, and preferably 5 to 10 mol of ethylene oxide onto the aforementioned partial glycerides are also suitable.

Sorbitan esters. Examples of suitable sorbitan esters include sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, as well as technical mixtures thereof. Addition products of 1 to 30, and preferably 5 to 10 mol of ethylene oxide onto the aforementioned sorbitan esters are also suitable.

Polyglycerol esters. Typical examples of suitable polyglycerol esters are polyglyceryl-2-dipolyhydroxystearate (Dehymuls® PGPH), polyglycerol-3-diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methyl glucose distearate (Tego Care® 450), polyglyceryl-3 beeswax (Cera Bellina@), polyglyceryl-4 caprate (polyglycerol caprate T2010/90), polyglyceryl-3 cetyl ether (Chimexane® NL), polyglyceryl-3 distearate (Cremophor® GS 32) and polyglyceryl polyricinoleate (Admul® WOL 1403) polyglyceryl dimerate isostearate, and mixtures thereof. Examples of further suitable polyol esters, optionally reacted with 1 to 30 mol of ethylene oxide, are mono-, di- and triesters of trimethylolpropane or pentaerythritol with lauric acid, coconut fatty acid, tallow fatty acid, palmitic acid, stearic acid, oleic acid, behenic acid and the like.

Anionic emulsifiers. Typical anionic emulsifiers are aliphatic fatty acids with 12 to 22 carbon atoms, such as palmitic acid, stearic acid, or behenic acid, as well as dicarboxylic acids with 12 to 22 carbon atoms such as azelaic acid or sebacic acid.

Amphoteric and cationic emulsifiers. In addition, zwitterionic surfactants may be used as emulsifiers. Zwitterionic surfactants are those surface-active compounds which bear at least one quaternary ammonium group and at least one carboxylate and one sulfonate group per molecule. Particularly suitable zwitterionic surfactants are the so-called betaines such as N-alkyl-N,N-dimethylammonium glycinates, for example cocoalkyl dimethylammonium glycinate, N-acylaminopropyl-N,N-dimethylammonium glycinates, for example cocoacylaminopropyl dimethylammonium glycinate, and 2-alkyl-3-carboxylmethyl-3-hydroxyethyl imidazolines, with in each case 8 to 18 carbon atoms in the alkyl or acyl group and cocoacylaminoethylhydroxyethylcarboxymethyl glycinate. Particularly preferred is the fatty acid amide derivative known by the CTFA name cocamidopropyl betaine. Ampholytic surfactants are also suitable emulsifiers. Ampholytic surfactants are understood to refer to those surface-active compounds which, in addition to one $C_{8/18}$-alkyl or acyl group per molecule, contain at least one free amino group and at least one —COOH or —$SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids with in each case approx. 8 to 18 carbon atoms in the alkyl group. Particularly preferred ampholytic surfactants are N-cocoalkylaminopropionate, cocoacylaminoethylaminopropionate and $C_{12/18}$-acylsarcosine. Finally, cationic surfactants may also be considered as emulsifiers, with those of the esterquat type, preferably methyl-quaternized difatty acid triethanolamine ester salts, being particularly preferred.

Fats and Waxes

Typical examples of fats are glycerides, i.e. solid or liquid vegetable or animal products which consist essentially of mixed glycerol esters of higher fatty acids, suitable waxes include natural waxes, for example candelilla wax, carnauba wax, Japan wax, esparto grass wax, cork wax, guaruma wax, rice germ oil wax, sugarcane wax, ouricury wax, montan wax, beeswax, shellac wax, spermaceti, lanolin (wool wax), uropygial fat, ceresin, ozokerite (earth wax), petrolatum, paraffin waxes, microcrystalline waxes; chemically modified waxes (hard waxes), for example montan ester waxes, sasol waxes, hydrogenated jojoba waxes, and synthetic waxes, for example polyalkylene waxes and polyethylene glycol waxes. In addition to the fats, suitable additives are also fat-like substances such as lecithins and phospholipids. The term lecithins is understood by the person skilled in the art to refer to those glycerophospholipids which form from fatty acids, glycerol, phosphoric acid and choline by esterification. Lecithins are thus frequently also referred to as phosphatidylcholines (PC). Examples of natural lecithins which may be mentioned are the cephalins, which are also referred to as phosphatidic acids and represent derivatives of 1,2-diacyl-sn-glycerol-3-phosphoric acids. In contrast, phospholipids are usually understood to mean mono- and preferably diesters of phosphoric acid with glycerol (glycerophosphates), which are generally considered to be fats. In addition, sphingosines and sphingolipids are also suitable.

Pearlescent Waxes

Examples of suitable pearlescent waxes include: alkylene glycol esters, specifically ethylene glycol distearate; fatty acid alkanolamides, specifically coconut fatty acid diethanolamide; partial glycerides, specifically stearic acid monoglyceride; esters of polyvalent, optionally hydroxy-substituted carboxylic acids with fatty alcohols having 6 to 22 carbon atoms, specifically long-chain esters of tartaric acid; fatty substances, for example fatty alcohols, fatty ketones, fatty aldehydes, fatty ethers, and fatty carbonates which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Cooling Agents

Cooling agents are compounds which produce a cool feeling on the skin. As a rule, these are menthol compounds which—in addition to the parent substance menthol itself—are selected for example from the group composed of menthol methyl ether, menthone glyceryl acetal (FEMA GRAS[1] 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl-N-ethyloxamate, monomethyl succinate (FEMA GRAS 3810), monomethyl glutamate (FEMA GRAS 4006), menthoxy-1,2-propanediol (FEMA GRAS 3784), menthoxy-2-methyl-1,2-propanediol (FEMA GRAS 3849) as well as the menthane carboxylic acid esters and amides WS-3, WS-4, WS-5, WS-12, WS-14 and WS-30, and mixtures thereof.

[footnote, pg. 9 ][1]FEMA stands for "Flavor and Extracts Manufacturers Association," and GRAS is defined as "Generally Regarded As Safe." A FEMA GRAS designation means that the substance so characterized has been tested by standard methods and found to be toxicologically safe.

A first important representative of these is monomenthyl succinate (FEMA GRAS 3810). Both the succinate and the analog monomenthyl glutarate (FEMA GRAS 4006) are important representatives of monomenthyl esters based on di- and poly-carboxylic acids:

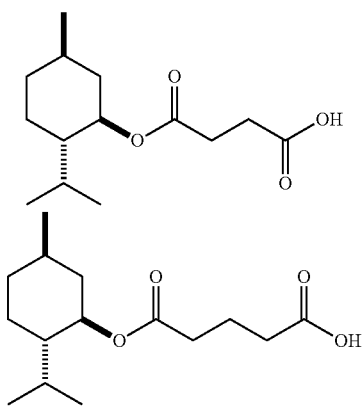

Examples of applications of these substances can be found for example in the documents WO 2003043431 (Unilever) or EP 1332772 A1 (IFF).

The next important group of preferred menthol compounds according to the invention comprises carbonate esters of menthol and polyols such as glycols, glycerol, or carbohydrates such as menthol ethylene glycol carbonate (FEMA GRAS 3805=Frescolat® MGC), menthol propylene glycol carbonate (FEMA GRAS 3784=Frescolat® MPC), menthol 2-methyl-1,2-propanediol carbonate (FEMA GRAS 3849), or the corresponding sugar derivatives. The menthol compounds menthyl lactate (FEMA GRAS 3748=Frescolat® ML), and in particular menthone glyceryl acetal (FEMA GRAS 3807) or menthone glyceryl ketal (FEMA GRAS 3808), which is marketed under the brand name Frescolat® MGA, are also preferred. Among these substances, menthone glyceryl acetal/ketal, menthyl lactate, and menthol ethylene glycol carbonate or menthol propylene glycol carbonate, which are marked by the applicant under the names Frescolat® MGA, Frescolat® ML, Frescolat® MGC, and Frescolat® MPC, have been found to be most particularly advantageous.

Menthol compounds, which have a C—C bond in the 3 position and also have a number of representatives suitable for use, were first developed in the 1970s. These are generally referred to as the WS type. The parent substance is a menthol derivative in which the hydroxyl group is replaced by a carboxyl group (WS-1). All other WS types are derived from this structure, such as the preferred species WS-3, WS-4, WS-5, WS-12, WS-14 and WS-30.

Bodying Agents and Thickeners

The main suitable bodying agents used are fatty alcohols or hydroxy fatty alcohols containing 12 to 22, and preferably 16 to 18 carbon atoms, as well as partial glycerides, fatty acids or hydroxy fatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil types (hydrophilic silicas), polysaccharides, in particular xanthan gum, guar-guar, agar-agar, alginates and tyloses, carboxymethylcellulose and hydroxyethyl and hydroxypropyl cellulose, also relatively high molecular weight polyethylene glycol monoesters and diesters of fatty acids, polyacrylates (for example, Carbopols® and Pemulen types from Goodrich]; Synthalens® from Sigma; Keltrol types from Kelco; and Sepigel types from Seppic; Salcare types from Allied Colloids), polyacrylamides, polymers, polyvinyl alcohol and polyvinyl pyrrolidone. Other bodying agents which have proved to be particularly effective are bentonites, for example Bentone® Gel VS-5PC (Rheox) which is a mixture of cyclopentasiloxane, disteardimonium hectorite, and propylene carbonate. Other suitable bodying agents are surfactants such as ethoxylated fatty acid glycerides, esters of fatty acids with polyols such as pentaerythritol or trimethylol propane, narrow-range fatty alcohol ethoxylates or alkyl oligoglucosides, and electrolytes such as sodium chloride and ammonium chloride.

Superfatting Agents and Stabilizers

As superfatting agents, substances such as lanolin and lecithin, as well as polyethoxylated or acylated lanolin and lecithin derivatives, polyol fatty acid esters, monoglycerides and fatty acid alkanolamides may be used, with the latter also serving as foam stabilizers. Metal salts of fatty acids, such as magnesium, aluminum and/or zinc stearate or ricinoleate, can be used as stabilizers.

Polymers

Suitable cationic polymers are, for example, cationic cellulose derivatives such as the quaternized hydroxyethyl cellulose obtainable from Amerchol under the name Polymer JR 400®, cationic starch, copolymers of diallyl ammonium salts and acrylamides, quaternized vinyl pyrrolidone/vinyl imidazole polymers such as Luviquat®(BASF), condensation products of polyglycols and amines, quaternized collagen polypeptides such as lauryldimonium hydroxypropyl hydrolyzed collagen (Lamequat® L, Grünau), quaternized wheat polypeptides, polyethyleneimine, cationic silicone polymers such as amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as quaternized chitosan, optionally in microcrystalline distribution, condensation products of dihaloalkylenes such as dibromobutane with bis-dialkylamines, for example bis-dimethylamino-1,3-propane, cationic guar gum such as Jaguar® CBS, Jaguar® C-17, and Jaguar® C-16 from Celanese, and quaternized ammonium salt polymers such as Mirapol® A-15, Mirapol® AD-1, and Mirapol® AZ-1 from Miranol.

Examples of suitable anionic, zwitterionic, amphoteric, and nonionic polymers include vinyl acetate-crotonic acid copolymers, vinyl pyrrolidone-vinyl acrylate copolymers, vinyl acetate-butyl maleate-isobornyl acrylate copolymers, methyl vinyl ether-maleic anhydride copolymers and esters thereof, uncrosslinked and polyol-crosslinked polyacrylic acids, acrylamidopropyl trimethylammonium chloride-acrylate copolymers, octylacrylamide-methyl methacrylate-tert-butylaminoethyl methacrylate-2-hydroxypropyl methacrylate copolymers, polyvinyl pyrrolidone, vinyl pyrrolidone-vinyl acetate copolymers, vinyl pyrrolidone-dimethylaminoethyl methacrylate-vinyl caprolactam terpolymers, and optionally derivatized cellulose ethers and silicones.

Silicone Compounds

Examples of suitable silicone compounds are dimethyl polysiloxanes, methylphenyl polysiloxanes, cyclic silicones, and amino-, fatty acid-, alcohol-, polyether-, epoxy-, fluorine-, glycoside-, and/or allyl-modified silicone compounds, which may be both liquid and resin-like at room temperature. Other suitable silicone compounds are simethicones which are mixtures of dimethicones with an average chain length of 200 to 300 dimethylsiloxane units and hydrogenated silicates.

UV Protection Factors

UV protection factors are understood for example to be organic substances which are liquid or crystalline at room temperature (light protection filters) and are capable of absorbing ultraviolet radiation and then releasing the energy absorbed in the form of longer-wavelength radiation, for example, heat. UV protection factors are usually present in amounts of 0.1 to 5, and preferably 0.2 to 1 wt %. UV-B filters can be oil-soluble or water-soluble. The following are examples of oil-soluble substances:

- 3-benzylidene camphor or 3-benzylidene norcamphor and the derivatives thereof, for example 3-(4-methylbenzylidene)-camphor;
- 4-aminobenzoic acid derivatives, preferably 4-(dimethylamino)benzoic acid-2-ethylhexyl ester, 4-(dimethylamino)benzoic acid-2-octyl ester, and 4-(dimethylamino)benzoic acid amyl ester;
- cinnamic acid esters, preferably 4-methoxycinnamic acid-2-ethylhexyl ester, 4-methoxycinnamic acid propyl ester, 4-methoxycinnamic acid isoamyl ester, and 2-cyano-3,3-phenylcinnamic acid-2-ethylhexyl ester (octocrylene);
- salicylic acid esters, preferably salicylic acid-2-ethylhexyl ester, salicylic acid-4-iso-propylbenzyl ester, and salicylic acid homomenthyl ester;
- derivatives of benzophenone, preferably 2-hydroxy-4-methoxybenzophenone, 2-hydroxy-4-methoxy-4'-methylbenzophenone, and 2,2'-dihydroxy-4-methoxybenzophenone;
- benzalmalonic acid esters, preferably 4-methoxybenzalmalonic acid di-2-ethylhexyl ester;
- triazine derivatives such as 2,4,6-trianilino-(p-carbo-2'-ethyl-1'-hexyloxy)-1,3,5-triazine and octyl triazone or dioctyl butamidotriazone (Uvasorb® HEB);
- propan-1,3-diones such as 1-(4-tert-butylphenyl)-3-(4'methoxyphenyl)propan-1,3-dione; and
- ketotricyclo(5.2.1.0)decane derivatives.

Suitable Water-Soluble Substances Include:

- 2-phenylbenzimidazol-5-sulfonic acid and alkali metal, alkaline earth metal, ammonium, alkylammonium, alkanolammonium, and glucammonium salts thereof;
- 1H-benzimidazole-4,6-disulfonic acid, 2,2'-(1,4-phenylene)bis-disodium salt (Neo Heliopan® AP);
- sulfonic acid derivatives of benzophenones, preferably 2-hydroxy-4-methoxybenzophenone-5-sulfonic acid and salts thereof;
- sulfonic acid derivatives of 3-benzylidene camphor such as 4-(2-oxo-3-bornylidenemethyl)-benzene sulfonic acid and 2-methyl-5-(2-oxo-3-bornylidene)-sulfonic acid and salts thereof.

Particular examples of typical UV-A filters include derivatives of benzoyl methane such as 1-(4'-tert-butylphenyl)-3-(4'-methoxyphenyl)-propane-1,3-dione, 4-tert-butyl-4'-methoxydibenzoyl methane (Parsol® 1789), 2-(4-diethylamino-2-hydroxybenzoyl)-benzoic acid hexyl ester (Uvinul® A Plus), 1-phenyl-3-(4'-isopropylphenyl)-propane-1,3-dione, and enamine compounds. The UV-A and UV-B filters may of course also be used in the form of mixtures. Particularly favorable combinations consist of the derivatives of benzoyl methane, for example 4-tert-butyl-4'-methoxydibenzoyl methane (Parsol® 1789) and 2-cyano-3,3-phenylcinnamic acid-2-ethyl hexyl ester (octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Such combinations are advantageously combined with water-soluble filters such as 2-phenylbenzimidazole-5-sulfonic acid and alkali metal, alkaline earth metal, ammonium, alkylammonium, alkanolammonium and glucammonium salts thereof.

In addition to the soluble substances mentioned above, insoluble light-blocking pigments, i.e. finely dispersed metal oxides or salts, may also be used for this purpose. Examples of suitable metal oxides are, in particular, zinc oxide and titanium dioxide, as well as oxides of iron, zirconium, silicon, manganese, aluminium and cerium and mixtures thereof. Silicates (talcum), barium sulfate, or zinc stearate may be used as salts. The oxides and salts are used in the form of the pigments for skin-care and skin-protecting emulsions and decorative cosmetics. The particles should have a mean diameter of less than 100 nm, preferably 5 to 50 nm, and more preferably 15 to 30 nm. They may be spherical in shape, but particles having an ellipsoid shape or deviating in any other way from a spherical shape may also be used. The pigments may also be surface-treated, i.e. hydrophilized or hydrophobized. Typical examples are coated titanium dioxides, for example Titanium Dioxide T 805 (Degussa) and Eusolex® T2000, Eusolex® T, Eusolex® T-ECO, Eusolex® T-S, Eusolex® T-Aqua, Eusolex® T-45D (all from Merck), and Uvinul TiO2 (BASF). Suitable hydrophobic coating materials are above all silicones, and among these, especially trialkoxyoctylsilanes or simethicones. So-called micro- or nanopigments are preferably used in sun protection products. Micronized zinc oxide such as Z-COTE® or Z-COTE HP1® is preferably used.

Humectants

Humectants are used to further optimize the sensory properties of the composition and for moisture regulation of the skin. At the same time, the low-temperature stability of the preparations according to the invention, in particular in the case of emulsions, is increased. Humectants are ordinarily contained in an amount of 0.1 to 15 wt %, preferably 1 to 10 wt %, and in particular 5 to 10 wt %.

Suitable humectants according to the invention include amino acids, pyrrolidone carboxylic acid, lactic acid and salts thereof, lactitol, urea and urea derivatives, uric acid, glucosamine, creatinine, decomposition products of collagen, chitosan or chitosan salts/derivatives, and in particular polyols and polyol derivatives (e.g. glycerol, diglycerol, triglycerol, ethylene glycol, propylene glycol, butylene glycol, erythritol, 1,2,6-hexanetriol, polyethylene glycols such as PEG-4, PEG-6, PEG-7, PEG-8, PEG-9, PEG-10, PEG-12, PEG-14, PEG-16, PEG-18, and PEG-20), sugar and sugar derivatives (such as fructose, glucose, maltose, maltitol, mannitol, inositol, sorbitol, sorbityl silanediol, sucrose, trehalose, xylose, xylitol, glucuronic acid and salts thereof), ethoxylated sorbitol (sorbeth-6, sorbeth-20, sorbeth-30, sorbeth-40), honey and hydrogenated honey, and hydrogenated starch hydrolysate, as well as mixtures of hardened wheat protein and PEG-20 acetate copolymer. According to the invention, particularly suitable humectants are glycerol, diglycerol, triglycerol, and butylene glycol.

Biogenic Active Ingredients and Antioxidants

Biogenic active ingredients are understood to refer, for example, to tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts such as prune extract and bambaranus extract, and vitamin complexes.

Antioxidants interrupt the photochemical reaction chain triggered when UV radiation penetrates the skin. Typical examples are amino acids (e.g. glycine, histidine, tyrosine, tryptophan) and the derivatives thereof, imidazole (e.g. urocanic acid) and the derivatives thereof, peptides such as D,L-carnosine, D-carnosine, L-carnosine and the derivatives thereof (e.g. anserine), carotenoids, carotenes (e.g. α-carotene, β-carotene, lycopene) and the derivatives thereof, chlorogenic acid and the derivatives thereof, lipoic acid and the derivatives thereof (such as dihydrolipoic acid), aurothioglucose, propylthiouracil and other thiols (such as thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl, and glyceryl esters thereof) and the salts thereof, dilauryl thiodipropionate, distearyl thiodipropionate, thiodipropionic acid and the derivatives thereof (esters, ethers, peptides, lipids, nucleotides, nucleosides and salts) and sulfoximine compounds (such as buthionine sulfoximine, homocysteine sulfoximine, buthionine sulfones, and penta-, hexa-, heptathionine sulfoximine) in very small compatible doses (such as pmol to μmol/kg), also (metal) chelating agents (such as α-hydroxy fatty acids, palmitic acid, phytic acid, lactoferrin), α-hydroxy acids (such as citric acid, lactic acid, malic acid), humic acid, bile acid, bile extracts, bilirubin, biliverdin, EDTA, EGTA and the derivatives thereof, unsaturated fatty acids and the derivatives thereof (such as γ-linolenic acid, linoleic acid, oleic acid), folic acid and the derivatives thereof, ubiquinone and ubiquinol and the derivatives thereof, vitamin C and derivatives (such as ascorbyl palmitate, Mg ascorbyl phosphate, ascorbyl acetate), tocopherols and derivatives (such as vitamin E acetate), vitamin A and derivatives (vitamin A palmitate) as well as coniferyl benzoate of benzoic resin, rutinic acid and the derivatives thereof, α-glycosyl rutin, ferulic acid, furfurylidene glucitol, carnosine, butylhydroxytoluene, butylhydroxyanisole, nordihydroguaiac resin acid, nordihydroguaiaretic acid, trihydroxybutyrophenone, uric acid and the derivatives thereof, mannose and the derivatives thereof, superoxide dismutase, zinc and the derivatives thereof (such as ZnO, $ZnSO_4$), selenium and the derivatives thereof (such as selenium methionine), stilbenes and the derivatives thereof (such as stilbene oxide, trans-stilbene oxide) and derivatives suitable according to the invention (salts, esters, ethers, sugars, nucleotides, nucleosides, peptides and lipids) of these active ingredients.

Hydrotropes

In order to improve flow behavior, hydrotropes such as ethanol, isopropyl alcohol, or polyols can also be used; these substances largely correspond to the carriers described above. Polyols that are suitable here preferably have 2 to 15 carbon atoms and at least two hydroxyl groups. The polyols can also contain further functional groups, in particular amino groups, or be modified with nitrogen. Typical examples are
  glycerol;
  alkylene glycols such as ethylene glycol, diethylene glycol, propylene glycol, butylene glycol, hexylene glycol, and polyethylene glycols with an average molecular weight of 100 to 1000 daltons;
  technical-grade oligoglycerol mixtures with an intrinsic degree of condensation of 1.5 to 10, such as technical-grade diglycerol mixtures with a diglycerol content of 40 to 50 wt %;
  methyol compounds, such as in particular trimethylolethane, trimethylolpropane, trimethylolbutane, pentaerythritol and dipentaerythritol;
  low alkyl glycosides, in particular those having to 8 carbon atoms in the alkyl radical, such as methyl and butyl glycoside;
  sugar alcohols having 5 to 12 carbon atoms, such as sorbitol or mannitol;
  sugars with 5 to 12 carbon atoms, such as glucose or saccharose;
  amino sugars, such as glucamine; and
  dialcohol amines, such as diethanolamine or 2-amino-1, 3-propanediol.

Preservatives

Examples of suitable preservatives include phenoxyethanol, formaldehyde solution, parabens, pentane diol or sorbic acid, the silver complexes known under the name Surfacine®, and the other classes of substances listed in Annex 6, Part A and B of the Cosmetics Ordinance.

Perfume Oils and Odorants

Perfume oils that may be mentioned are mixtures of natural and synthetic odorants. Natural odorants are extracts from flowers (lily, lavender, rose, jasmine, neroli, ylang ylang), stems and leaves (geranium, patchouli, petitgrain), fruits (anise, coriander, cumin, juniper), fruit peels (bergamot, lemon, orange), roots (maize, angelica, celery, cardamom, costus, iris, calmus), woods (pinewood, sandalwood, guaiac wood, cedar wood, rosewood), herbs and grasses (tarragon, lemon grass, sage, thyme), needles and branches (spruce, fir, pine, dwarf-pine), and resins and balsams (galbanum, elemi, benzoe, myrrh, olibanum, opoponax). Animal raw materials such as civet and castoreum are also suitable. Typical synthetic fragrance compounds are products of the ester, ether, aldehyde, ketone, alcohol and hydrocarbon types. Fragrance compounds of the ester type include benzyl acetate, phenoxyethyl isobutyrate, p-tert-butyl cyclohexyl acetate, linalyl acetate, dimethyl benzyl carbinyl acetate, phenylethyl acetate, linalyl benzoate, benzyl formate, ethyl methylphenyl glycinate, allyl cyclohexylpropionate, styrallyl propionate and benzyl salicylate. The ethers include benzyl ethyl ethers, the aldehydes include linear alkanals having 8 to 18 carbon atoms, citral, citronellal, citronellyloxyacetaldehyde, cyclamen aldehyde, hydroxycitronellal, lilial and bourgeonal, the ketones include the ionones, α-isomethyl ionone and methyl cedryl ketone, the alcohols include anethole, citronellol, eugenol, isoeugenol, geraniol, linalool, phenylethyl alcohol and terpineol, and the hydrocarbons include primarily the terpenes and balsams. Preferably, however, preference mixtures of different odorants which together produce a pleasant scent note are used. Essential oils of lower volatility, which are mostly used as fragrance components, are also suitable as perfume oils, e.g. sage oils, camellia oil, clove oil, melissa oil, mint oil, cinnamon leaf oil, linden blossom oil, juniper berry oil, vetiver oil, olibanum oil, galbanum oil, labolanum oil, and lavandin oil. Preferably, bergamot oil, dihydromyrcenol, lilial, lyral, citronellol, phenylethyl alcohol, α-hexylcinnamaldehyde, geraniol, benzyl acetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, vertofix Coeur, iso-E-Super, Fixolide NP, evernyl, iraldein gamma, phenylacetic acid, geranyl acetate, benzyl acetate, rose oxide, Romilat, Irotyl and Floramat are used alone or in mixtures.

Examples of suitable flavoring agents include peppermint oil, spearmint oil, anise oil, star anise oil, cumin oil, *eucalyptus* oil, fennel oil, lemon oil, wintergreen oil, clove oil, menthol and the like.

Dyes

Substances that are suitable and approved for cosmetic purposes can be used as dyes, such as those listed in the publication "Cosmetic Coloring Agents" of the Colorant Commission of the German Research Foundation, Verlag Chemie, Weinheim, 1984, pp. 81-106. Examples include Cochineal Red A (C.I. 16255), Patent Blue V (C.I. 42051), indigotin (C.I. 73015), chlorophyllin (C.I. 75810), Quinoline Yellow (C.I. 47005), titanium dioxide (C.I. 77891), Indanthrene Blue RS (C.I. 69800) and madder lake (C.I. 58000). Luminol can also be included as a luminescent dye. These dyes are ordinarily used in concentrations of 0.001 to 0.1 wt %, relative to the total mixture.

The total amount of the auxiliary substances and additives can be 1 to 50, and preferably 5 to 40 wt % relative to the dyes. The production of the dyes can be carried out by common cold or hot processes; the phase inversion temperature method is preferred.

Screening Method

A further object of the invention relates to a method for identifying active ingredients that promote or accelerate wound healing, in which (a) a keratinocyte culture is provided that contains the olfactory receptor OR2AT4,
(b) the active ingredient to be tested is added to the culture, and
(c) the change in intracellular calcium concentration is determined.

It is likely that an active ingredient will be capable of supporting or even accelerating wound healing if the receptor is activated by the active ingredient, resulting in increased calcium secretion in the cells, preferably HaCaT cells. This is in particularly the case if each administration of the active ingredient increases the amplitude of the calcium concentration compared to the previous administration.

Examples

Characterization of OR2AT4 in the Heterologous Expression System

In order to elucidate the function of a receptor in a tissue, it is important to identify the ligands in order to ensure that the receptor can be activated in the native system. Most ORs have not yet been deorphanized. For this reason, OR2AT4, which was identified in human keratinocytes, was first more precisely characterized in a heterologous expression system, and the receptive field was determined.

Heterologous Expression of OR2AT4 in Hana3A Cells

Hana3A cells expressing stable endogenous olfactory transduction factors, which specifically target the incorporation of ORs into the cell membrane and thus improve activation capacity, were used as a heterologous expression system. Moreover, the 20 first N-terminal amino acids of rhodopsins (Rho-tag) were added before the N-terminus of the coding sequence of the OR, also in order to support heterologous expression.

In order to detect the heterologous expression of OR2AT4 in Hana3A cells, these cells were transfected with the receptor plasmid (pcDNA3-OR2AT4) for 48 hours by the calcium phosphate method, and immunocytochemical staining was carried out with an OR2AT4-specific antibody ($\alpha$-OR2AT4 antibody) and a rhodopsin-specific antibody ($\alpha$-Rho antibody). The clearly visible costaining of the two antibodies made it possible to show that $\alpha$-OR2AT4 antibody specifically binds to the receptor, and that heterologous expression of the receptor in Hana3A cells is possible. The N-terminus of the coding sequence of the OR was attached, also in order to support heterologous expression. In order to detect the heterologous expression of OR2AT4 in Hana3A cells, these cells were transfected with the receptor plasmid (pcDNA3-OR2AT4) for 48 hours by the calcium phosphate method, and immunocytochemical staining was carried out with an OR2AT4-specific ($\alpha$-OR2AT4 antibody) and a rhodopsin-specific antibody ($\alpha$-Rho antibody). The clearly visible costaining of the two antibodies made it possible to show that $\alpha$-OR2AT4 antibody specifically binds to the receptor, and that heterologous expression of the receptor in Hana3A cells is possible (FIG. 1, top).

It was possible to rule out non-specific binding of $\alpha$-OR2AT4 antibody by means of control stains with another heterologously expressible OR, OR1A2. In Hana3A cells transfected with OR1A2, clear rhodopsin staining showed the expression of the receptor, but staining of the $\alpha$-OR2AT4 antibody was not identifiable (FIG. 1, bottom). As a further control, Hana3A cells were incubated without the primary antibody in order to rule out non-specific binding of the secondary antibody.

Membrane Expression of OR2AT4 in Hana3A Cells

In order to ensure the binding of extracellular ligands to the OR2AT4 heterologously expressed in Hana3A cells, said receptor must be incorporated into the plasma membrane. It is known that ORs can only be expressed with extreme difficulty in the heterologous system, which is often deficient in transporting the receptors from the endoplasmic reticulum to the cell surface. It is therefore essential to verify incorporation of the receptor into the membrane and determine the transfection rate before carrying out deorphanization studies. For this purpose, live cell staining according to Zhang and Matsunami (2008) was carried out, in which only surface proteins can be selectively stained, as the cell membrane is not permeabilized.

Figure 2:
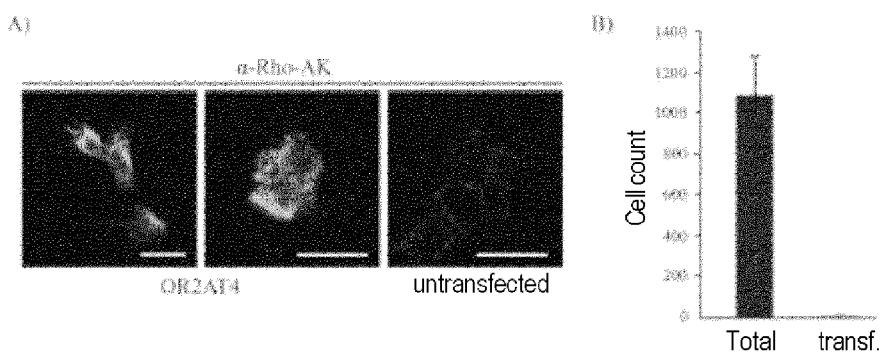

$\alpha$-Rho antibody, which detects the N-terminal Rho tag of the recombinantly expressed OR, was again used for staining. The staining showed that after 48-hour transfection by the calcium phosphate method, OR2AT4 is successfully incorporated into the membrane (FIG. 2a). By determining the number of stained Hana3A cells (mean=12 cells) relative to the total cell count (mean=1050 cells), the transfection rate was found to be approx. 1.3% (FIG. 2b).

In summary, the present results show that OR2AT4 is expressed in Hana3A cells in a membrane-bound manner, and the requirements for characterization of the receptive field of the receptor were therefore met.

The Receptive Field of Recombinantly Expressed OR2AT4

A method established at the Department of Cell Physiology of Ruhr University Bochum for deorphanization studies is calcium imaging, in which activation of an OR by an odorant is visualized by a change in the intracellular calcium concentration of transfected cells using a fluorescent dye [cf. Wetzel et al. in: J. Neurosci. 19, pp. 7426-7433 (1999); Spehr et al. in: Science 299, pp. 2054-2058 (2003); Neuhaus et al. in: J. Biol. Chem. 284, pp. 16218-16225 (2009)]. In this method, the Hana3A cells are briefly (20 s) stimulated with an odorant and selected for odorant screenings of high concentrations (up to 1 mM) in order to confirm activation of ORs weakly expressed in Hana3A cells.

Investigation of potential agonists of recombinantly expressed OR2AT4.

Figure 3:
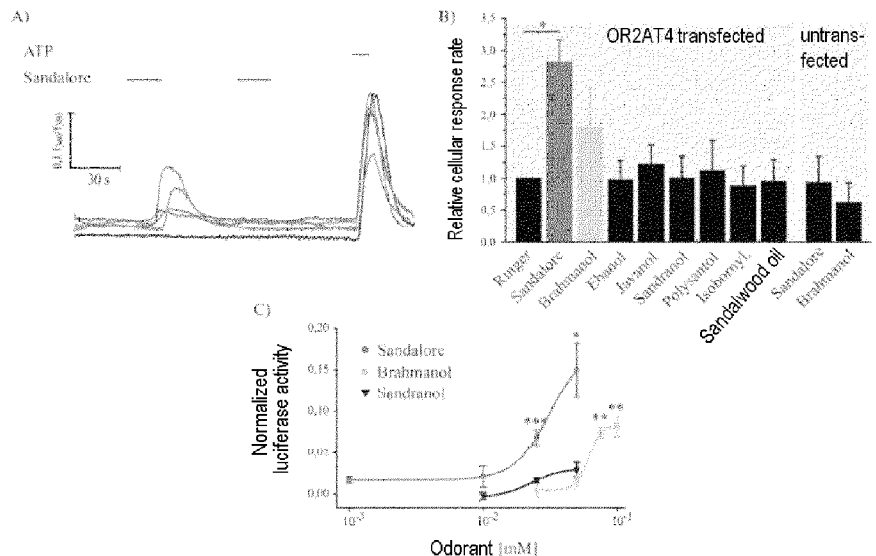

The activation of OR2AT4 by Sandalore® was first investigated by the calcium imaging method. On stimulation with 1 mM of Sandalore®, transient OR2AT4-transfected Hana3A cells showed specific calcium signals, with the cells being activatable by the sandalwood odor only once (FIG. 3a). In quantification, a significantly increased response rate of the Hana3A cells relative to the Ringer control was observed, which confirms the activation of the receptor by the sandalwood odor. As a receptor can often be activated by multiple structurally related molecules, OR2AT4 was stimulated with six further synthetic sandalwood odorants (Brahmanol, Ebanol, isobornyl cyclohexanol, Javanol, Polysantol, and Sandranol) and with natural sandalwood oil, and activation of the receptor was observed. In this case, only Brahmanol showed an increased response rate in calcium imaging experiments, although the increase was not significant (FIG. 3b).

By conducting control measurements of untransfected Hana3A cells, the possibility that the increased response rates of the two sandalwood odorants is caused by direct activation of the Hana3A cells was ruled out (FIG. 3b, right).

In order to verify calcium imaging results and investigate dose-dependent activation of OR2AT4, a further method of deorphanization based on a dual luciferase system was used. In this method, in addition to the OR, two luciferases were introduced into the Hana3A cells. When the expressed OR is activated by an odorant and cAMP is formed in the further course of the signal cascade, this initiates expression of firefly luciferase via CRE (cAMP response elements). The second luciferase, *Renilla* luciferase, serves as a control for transfection and vitality of the cells. By calculating the two luciferase values, the activation capacity of an OR by an odorant can be determined. In the CRE luciferase assay, the odorant remains on the cells for hours in order to ensure that the luciferase is expressed. Because of the longer incubation time of the odorants and the possibility of activating more receptors in a 96-well format, this method is more sensitive than calcium imaging and is well-suited for establishing dose-response relationships.

In the CRE luciferase assay, Sandalore® and Brahmanol® showed significant dose-dependent activation of the recombinant receptor expressed in Hana3A cells. For Brahmanol, however, a higher concentration (≥75 µM) was required than for Sandalore® (≥25 µM) in order to produce a significant effect at the receptor (FIG. 3c). Sandranol®, which on the other hand showed no reaction at the investigated concentration (≥50 µM), was used as a further sandalwood odorant (FIG. 3c).

As the 4-hour incubation in the luciferase assay caused the odorants, from a certain concentration on, to have a toxic effect on the Hana3A cells, no higher odorant concentrations (Sandalore®≤50 µM, Brahmanol®≤100 µM, Sandranol®≤50 µM) could be used, and thus no complete dose-response curves could be prepared. This toxicity manifested itself inter alia in reduced values of the control reporter *Renilla* luciferase. For this reason, only values with uniformly high *Renilla* signals were used for evaluation (Zhuang and Matsunami, 2008). For the sandalwood odorants Javanol, Polysantol, isobornyl cyclohexanol, and sandalwood oil, the highest useable concentrations were 10-25 µM. However, no increased activation of OR2AT4 was seen up to this concentration.

Investigation of potential antagonists of recombinantly expressed OR2AT4.

Odorants can not only activate a receptor, but can also act as antagonists to an OR. Using the calcium imaging technique, the odorants Oxyphenylon and Phenirat were identified as antagonists that significantly reduced Sandalore®-induced calcium signals in coapplication with Sandalore® (1:1, 1 mM respectively). The odorant dimetol, which had no effect on the Sandalore®-induced calcium signals in combined application, was used as a control. Dimetol, Phenirat, and Oxyphenylon alone showed no effect on the Hana3A cells.

Figure 5:
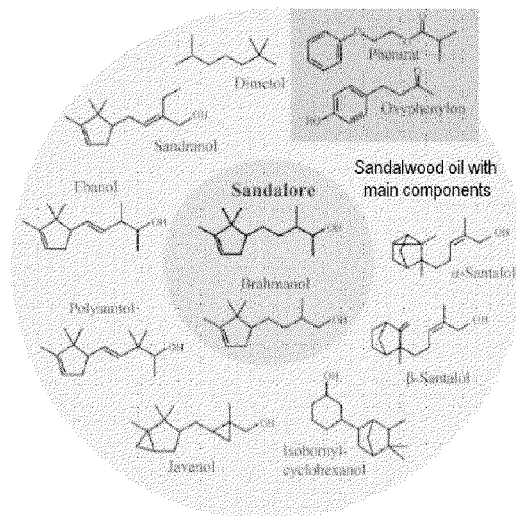

In summary, Sandalore® and Brahmanol® were found to be agonists and Oxyphenylon and Phenirat were found to be antagonists to heterologously expressed OR2AT4. The receptive field of OR2AT4 and the structural formulae of the investigated odorants are graphically shown in FIG. 5.

Detection of Expression of OR2AT4 in Human Keratinocytes

RT-PCR analyses were conducted for identification of ectopic expression of OR2AT4 in various human skin cell types and tissues. In addition, the expression analyses of OR2AT4 in human keratinocytes were supplemented by immunocytochemical staining.

Expression of OR2AT4 in Human Skin Cells and Tissues by RT-PCR

Figure 6:
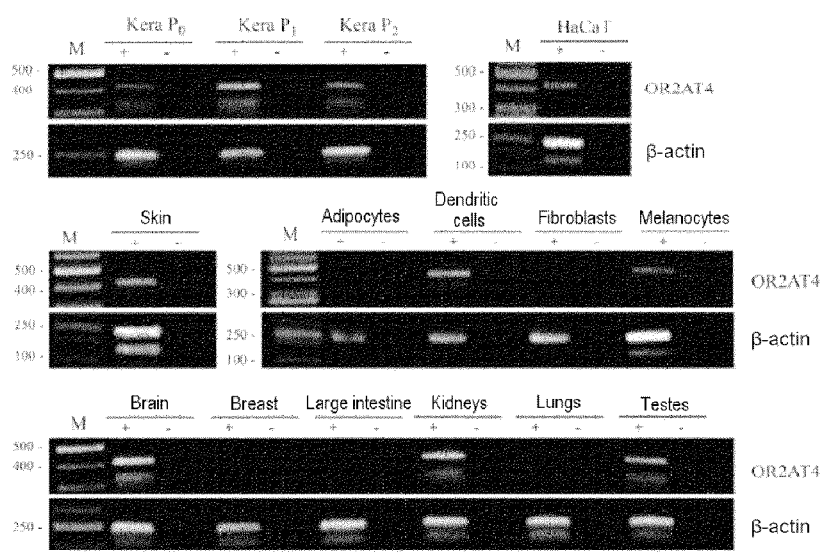

For detection of OR2AT4 at the transcript level, RNA of various skin cell types and skin biopsy specimens was isolated, and RT-PCR was carried out. Transcripts of OR2AT4 were detected in human primary keratinocytes of various differentiation stages, HaCaT cells, and human skin biopsy specimens (full thickness skin) (FIG. 6). As human skin, in addition to the main component of keratinocytes, also consists of further cells such as connective tissue, pigment, and immune cells, the cell types were individually investigated by RT-PCR for expression of the receptor. It was found that dendritic cells and melanocytes also express OR2AT4. In contrast, no expression of the receptor was detected in adipocytes or fibroblasts (FIG. 6, center).

In order to determine whether the receptor is exclusively expressed in the skin, total RNA samples of various human tissues (brain, breast, colon, kidneys, lungs, and testes) were used for further RT-PCR analyses. It was found that OR2AT4 is not exclusively expressed in the skin, but is also expressed other tissues such as the brain, kidneys and testes. In the breast, large intestine, and lungs, on the other hand, no transcripts were detected (FIG. 6, bottom). In order to rule out the possibility that PCR products were not detected because of poorly isolated or degraded RNA, a β-actin control was carried out for of the all samples to confirm RNA quality, and this control was positive in all RNA samples (FIG. 6).

Detection of OR2AT4 Expression in Human Keratinocytes by Immunocytochemistry

Figure 7:
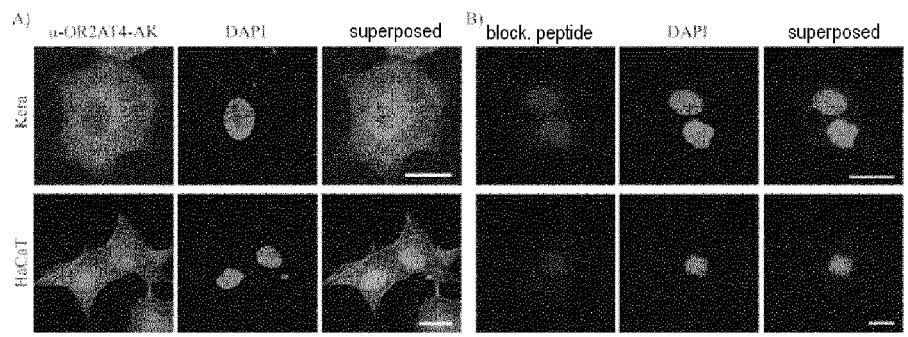

In order to detect the expression of OR2AT4 at the protein level, immunocytochemical stains were carried out with a self-generated α-OR2AT4 antibody. The specificity of the antibody was investigated in Hana3A cells transiently transfected with OR2AT4. In use of the α-OR2AT4 antibody, clear staining of the HaCaT cells and the keratinocytes was visible in the confocal immunofluorescence images (FIG. 7a)

In order to rule out non-specific binding of the antibody to skin cells, a blocking peptide was used. This peptide blocks the α-OR2AT4 antibody, which can then no longer attach to the binding site. With use of the blocking peptide, only slight staining of the cell nucleus and the areas around the nucleus could be seen (FIG. 7b). As a further control, the cells were incubated without the primary antibody in order to rule out non-specific binding of the secondary antibody (data not shown). The binding of α-OR2AT4 antibody is therefore specific, and expression of the receptor at the protein level was confirmed in human keratinocytes.

Figure 8:
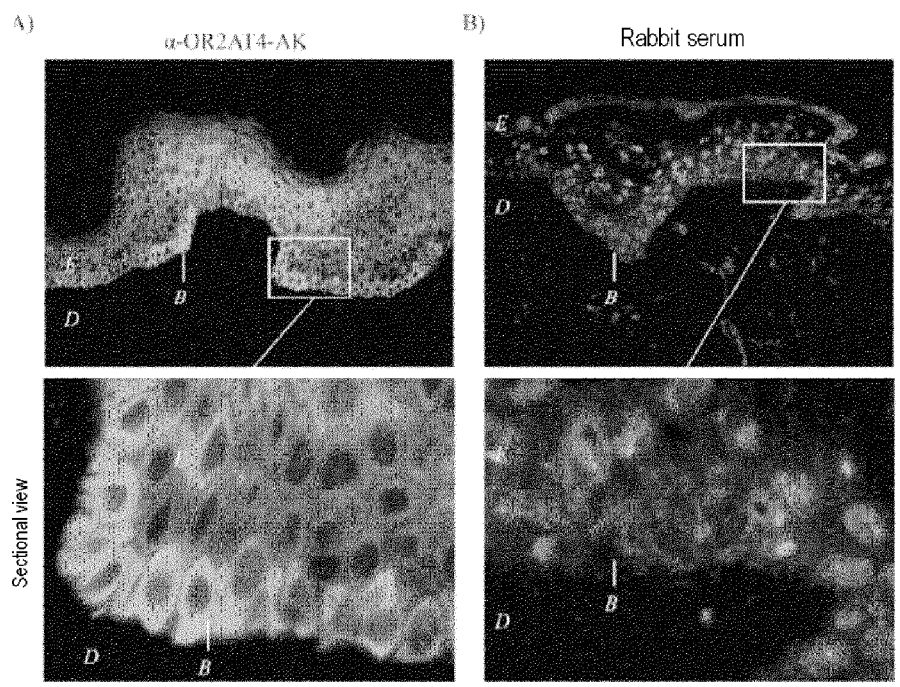

In addition to cultivated keratinocytes, the protein expression of OR2AT4 in the human skin was investigated. For this purpose, skin sections were also stained with α-OR2AT4 antibody. Clear expression of the receptor in epidermal keratinocytes was identifiable in the stains (FIG. 8a, top), with basal keratinocytes showing the strongest antibody binding (FIG. 8a, sectional view). The dermis, located under the epidermis, showed no specific staining. There was also no specific staining observed in control stains, in which the primary antibody was replaced with rabbit serum (FIG. 8b).

Characterization of Sandalore®-Induced Calcium Signals in Human Keratinocytes

In characterization of the physiological function of OR2AT4 in skin cells, it is important to investigate the activation capacity of this receptor by the identified ligands Sandalore® and Brahmanol® in human cultivated keratinocytes. In this part of the investigation, the focus was on the ligand Sandalore®.

In calcium imaging experiments, 80-90% of the HaCaT cells and the primary keratinocytes are repeatedly simulated by Sandalore®, with the Sandalore-induced calcium signals showing significant sensitization, i.e. an increase in signal amplitude after each further application showed (FIGS. 9a and 9b).

More precise investigation of the amplitude of the first application showed dose-dependent activation of the HaCaT cells by Sandalore®, beginning at 100 µM and reaching saturation from approx. 2 mM (FIG. 9c). In the fourth application, saturation occurred at approx. 500 µM (FIG. 9d). The ECR50R value was 430 µM of Sandalore® in the first application and 112 µM of Sandalore® in the fourth application.

Investigation of Sensitizing of Sandalore®-Induced Calcium Signals

Figure 9:
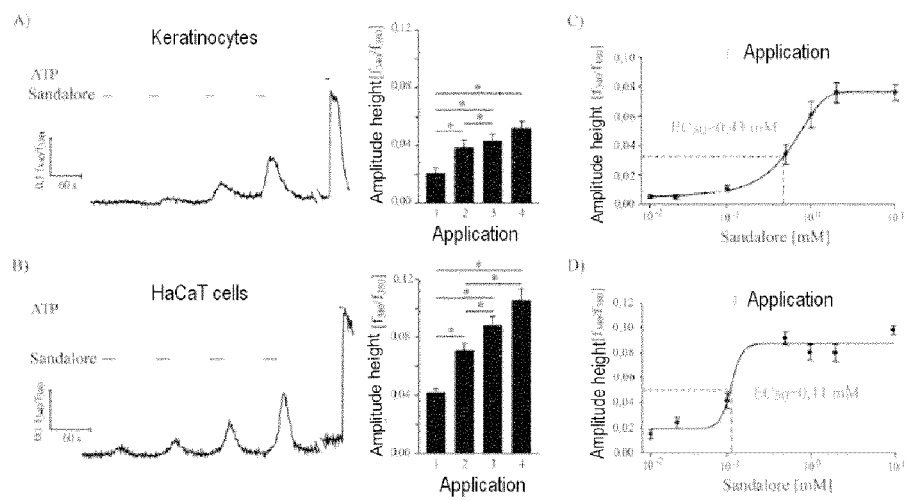

For Sandalore®-induced calcium signals, the increase in amplitudes with repeated stimulation is characteristic (FIG. 9). In order to investigate the role of cell-cell channels (gap junctions), through which keratinocytes can exchange molecules such as ATP or Ca$^{2+}$, in this sensitization mechanism, the two gap junction blockers 1-octanol and carbenoxolone were used.

Figure 10:
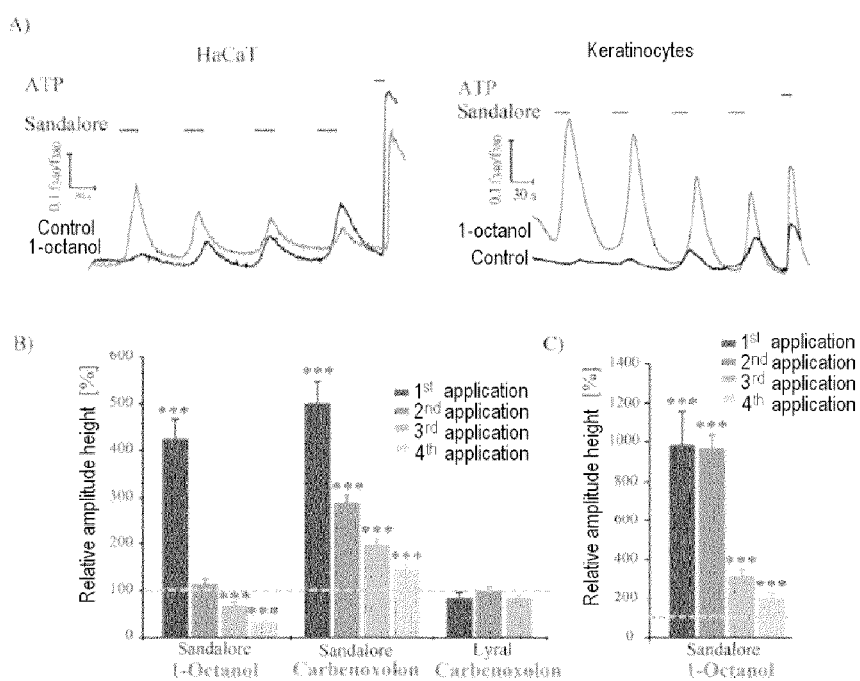

After preincubation of keratinocytes or HaCaT cells with the blocker 1-octanol, enhancement of the Sandalore®-induced calcium signals could be identified in calcium imaging experiments (FIG. 10a). Quantification of the results showed that the first amplitude induced by Sandalore® with use of 1-octanol was increased in HaCaT by approx. 400% (FIG. 10b) and in keratinocytes by almost 1000% (FIG. 10c). The subsequent calcium signals continually decreased on repeated Sandalore® stimulation compared to the control measurements. Use of the second gap junction blocker carbenoxolone produced the same result (FIG. 10b).

In order to rule out the possibility that non-specific effects occurred due to blocking of the gap junctions, after preincubation with carbenoxolone, the cells were also stimulated with Lyral, a further odorant that induces calcium signals in skin cells. No effect on the Lyral-induced response pattern was seen (FIG. 10b).

Pharmacological Characterization of Sandalore®-Induced Calcium Signals

Figure 11:
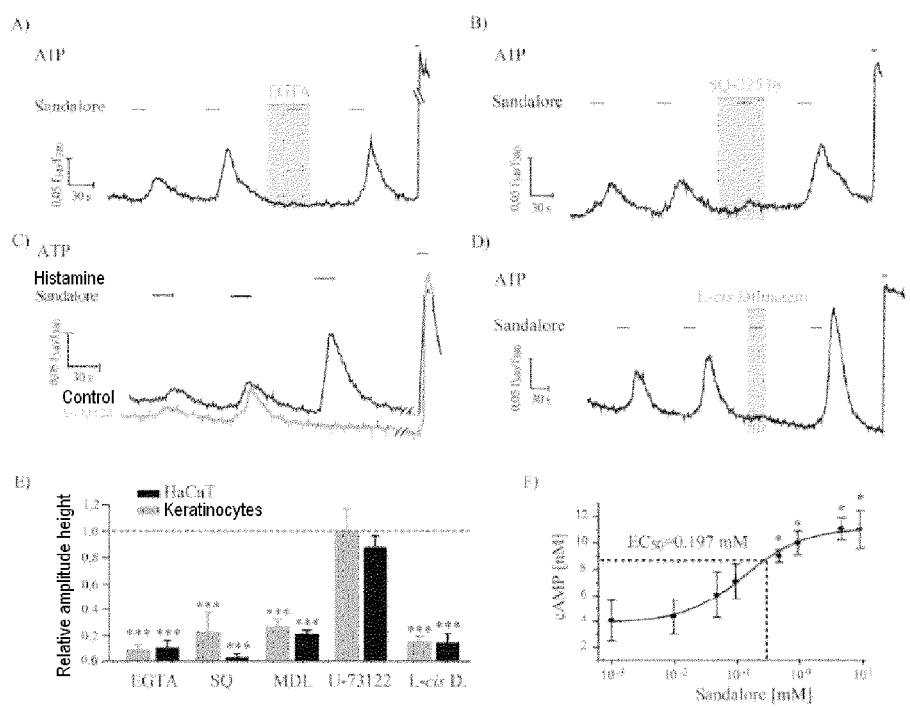

The Sandalore®-induced signal cascade in HaCaT cells and primary keratinocytes was pharmacologically characterized using the calcium imaging technique and specific blockers of signal cascade proteins. An investigation was first conducted in order to determine whether the calcium signals are caused by calcium inflow from the extracellular space. For this purpose, a calcium-free extracellular solution was used with a calcium chelator (EGTA) added. In the presence of the calcium-free solution, Sandalore®-induced calcium signals were significantly reduced (FIGS. 11a and 11e). In order to investigate the role of adenylyl cyclase, the specific blockers SQ-22536 and MDL-12330A were used. In this case as well, a significant reduction in Sandalore-induced calcium signals was observed in the presence of the respective blockers (FIGS. 11b and 11e). On the other hand, participation of phospholipase C was ruled out, as the PLC blocker U-73122 showed no effect on Sandalore®-induced calcium signals (FIGS. 11c and 11e). The efficacy of the blockers was tested in this case with histamine, which activated the PLC signalling pathway (FIG. 11c).

In order to identify the calcium channel through which calcium ions flow from the outside into the cytosol of the skin cells, the CNG channel blocker L-cis-diltiazem was used. This substance also significantly reduced Sandalore®-induced calcium signals (FIGS. 11d and 11e). An additional cAMP assay was conducted in order to verify the data of pharmacological characterization by means of the calcium imaging technique. For this purpose, HaCaT cells with various Sandalore® concentrations were stimulated, and cAMP content was determined. The results showed a dose-dependent cAMP increase, with an EC50 value of 197 µM of Sandalore® (FIG. 11f).

In summary, a cAMP-dependent signalling pathway with participation of a CNG channel was therefore established for the Sandalore®-induced calcium signals of the HaCaT cells and primary keratinocytes.

Expression of Olfactory Signal Cascade Components and Structurally Related Proteins In sperm cells and the kidneys, in addition to functional ectopic expression of ORs, additional components of the olfactory signal cascade, such as the subunit of the olfactory G-protein G■olf and adenylyl cyclase 3 (AC3), were detected. Moreover, in addition to ectopic expression of OR, studies show extensive distribution of the components of the olfactory signal cascade in a wide variety of tissues. In this investigation, therefore, an overview was obtained of the signal cascade proteins expressed in the keratinocytes and involved in the olfactory signal cascade by means of transcriptome analysis (next generation sequencing, NGS).

Expression of Olfactory Signal Cascade Components and Structurally Related Proteins at the Transcript Level.

NGS data of primary keratinocytes were evaluated in order to investigate the signal cascade proteins. In addition to the components occurring in the olfactory signal cascade, such as Gαolf, AC3, CNGA2 and TMEM16B, further structurally related signal cascade proteins were also investigated. By evaluating transcriptome data of the primary keratinocytes, expression of the subunits of Gαolf (FPKM=3.6) and AC3 (FPKM=2.1) could be confirmed. The expression field was rather small compared to that of related proteins such as the subunit of the stimulatory G-protein Gαs (FPKM=69.2) or AC6 (FPKM=14.1).

Figure 12:
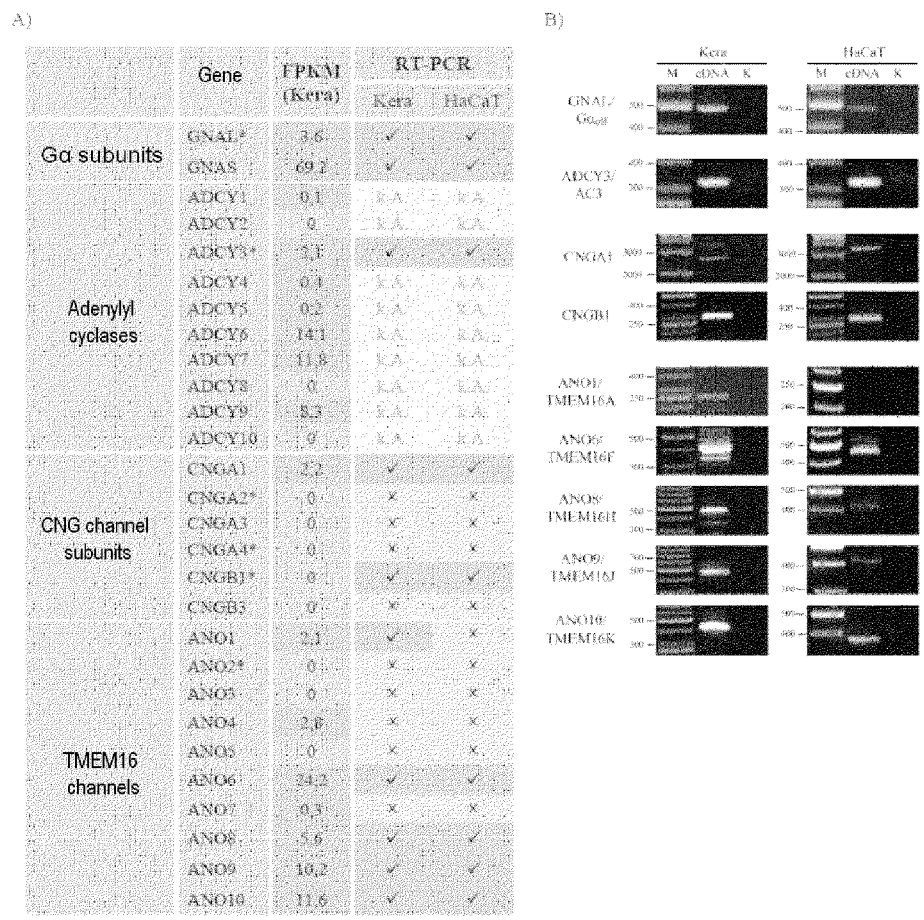

Moreover, transcripts of the CNG channel subunit CNGA1 (FPKM=2.2) and seven of the ten investigated representatives of the chloride channel family TMEM16 were detected in keratinocytes (FIG. 12a). For validation of the NGS data, RT-PCR experiments were conducted with primary keratinocytes and HaCaT cells (FIG. 12b). The expression of Gαolf and AC3 was confirmed for both cell types. Moreover, expression of the chloride channels TMEM16H, TMEM16J, TMEM16F, TMEM16K, and the CNGA1 subunit were detected both in the primary keratinocytes and in the HaCaT cells. The NGS data used here show low sequencing depth (≈18 million reads), so it was possible that low-expression genes could not be detected by this method. For this reason, some of the genes not expressed according to NGS data were also investigated by RT-PCR.

In this case it was found that in addition to the CNGA1 subunit, the CNGB1 subunit is also expressed in HaCaT cells and keratinocytes.

Expression of Components of the Olfactory Signal Cascade and Structurally Related Proteins at the Protein Level.

Figure 13:
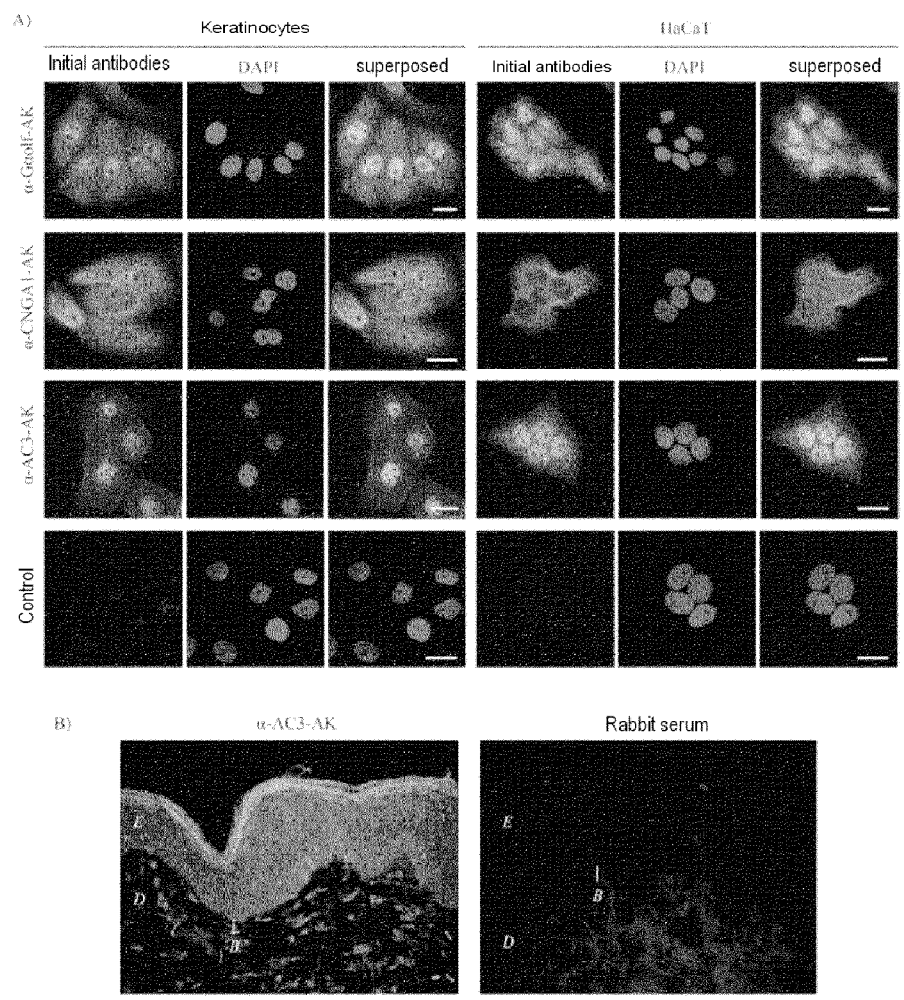

In addition to RT-PCR experiments, immunocytochemical stains for detecting the components of the olfactory signal cascade Gαolf, RAC3, and CNGA1 were also prepared with HaCaT cells and primary keratinocytes. For both cell types, clear expression of Gαolf, AC3, and CNGA1 was seen on the immunocytochemical stains (FIG. 13a). The Gαolf and AC3 stains showed clear nuclear staining in addition to cytosolic location. Proteins without primary antibodies were used as a control, showing no non-specific binding of the secondary antibody.

In addition to the cultivated keratinocytes, detection of Gαolf was carried out in advance by means of immunocytochemical staining of skin sections. In order to complete the data, human skin sections were stained with α-AC3 antibody. This showed strong expression of AC3 in epidermal keratinocytes. Control stains, in which the primary antibody was replaced with rabbit serum, showed no specific staining (FIG. 13b).

Role of OR2AT4 in Sandalore-Induced Calcium Signals in Human Keratocytes

Human keratinocytes express the receptor OR2AT4 and show calcium signals on stimulation with the ligand Sandalore®. In order to investigate whether the Sandalore®-induced calcium signals are transmitted via OR2AT4 and not via another receptor or mechanism, RNA interference experiments on the one hand and tests of the above-described antagonists of OR2AT4 are carried out.

RNA Interference Experiments

In RNA interference, a small interfering RNA (siRNA) is introduced into a cell, causing the mRNA having the complementary 1T2T 1T2T nucleotide sequence of the siRNA to be broken down, and the corresponding coded 1T2T 11 protein 11, i.e. 1T2T, is no longer synthetized. For the RNA interference experiments conducted here, two self-generated siRNAs were used that are directed against OR2AT4. If the action of the siRNA is successful, the mRNA of OR2AT4 is broken down, with the result that no functional receptor protein is translated, and as a result, the Sandalore®-induced calcium signals should be reduced.

In order to exclude non-specific effects, two control siRNAs (scRNAs) that were not thought to have any effect on the cells were used. First, a control experiment was conducted with Hana3A cells to determine whether the two self-generated siRNAs would successfully cause degradation of the transcripts of OR2AT4. For this purpose, Hana3A cells were cotransfected with a special luciferase- and OR2AT4-expressing reporter plasmid (pmirGLO-OR2AT4) and the respective siRNA or scRNA. If the mRNA of OR2AT4 is degraded by the siRNA, the mRNA of the luciferase is destroyed by a fusion mRNA of luciferase and OR2AT4, and the luminescent signal is reduced as a result.

Figure 14:
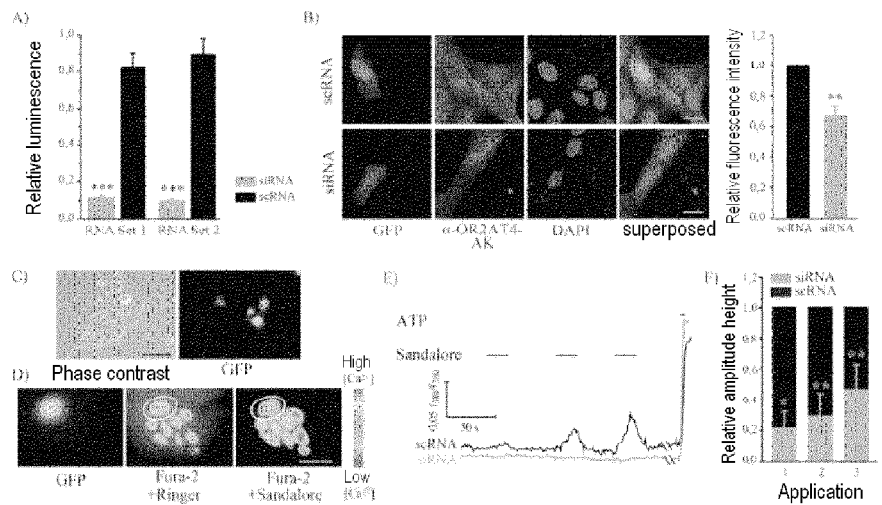

The results showed that the two siRNA variants caused degradation of the transcripts of OR2AT4, as clearly shown by the significant reduction in the luminescence signal. The two scRNAs showed no effect (FIG. 14a). The requirements for successful knockdown experiments were therefore met, and it was possible to carry out functionality experiments on HaCaT. It was first investigated whether the expression of OR2AT4 is reduced by siRNA in HaCaT cells as well. For this purpose, HaCaT cells were transfected for two days with a mixture of the two siRNAs or scRNAs, and immunocytochemical stains in which the specific OR2AT4 antibody was used were carried out. HaCaT cells that had successfully taken up the siRNA of scRNA could be identified by means of GFP, which is also expressed via the pGeneClip vector. Comparison of the α-OR2AT4 antibody stains of siRNA or scRNA-expressing cells showed that staining, and thus the expression of OR2AT4, was significantly reduced in use of siRNA, and that siRNA is therefore functional in HaCaT cells as well (FIG. 14b).

In order to determine whether the OR2AT4 plays a role in Sandalore®-induced calcium signals, HaCaT cells were transfected for two days with a mixture of the two RNAs, siRNA or scRNA (FIG. 14c), and used in calcium imaging experiments. During the measurements, it was possible to distinguish between siRNA- or scRNA-expressing and non-expressing cells based on the coexpression of GFP (FIG. 14d). The transfected cells were repeatedly stimulated with Sandalore®, and the amplitudes of the calcium signals were calculated. The HaCaT cells transfected with siRNA showed a significant reduction in Sandalore®-induced calcium signals relative to the scRNA-expressing cells for all three Sandalore® applications (FIGS. 14e and 14f).

Action of Antagonists on Sandalore®-Induced Calcium Signals in Human Keratinocytes By means of antagonists, the activation of a receptor by its specific ligands can also be verified, as the inhibition of the ligand-induced calcium signal in the heterologous system and in the native cells appears to indicate activation of the same receptor. As described above, Phenirat and Oxyphenylon were identified for OR2AT4 as antagonists that respectively inhibited Sandalore®-induced calcium signals in the heterologous system in combined application. Dimetol, which showed no inhibitory effect in coapplication with Sandalore®, was used as a control. The two antagonists were therefore to be tested for potential inhibition of Sandalore®-induced calcium signals in HaCaT cells in order to investigate the involvement of OR2AT4.

Figure 15:
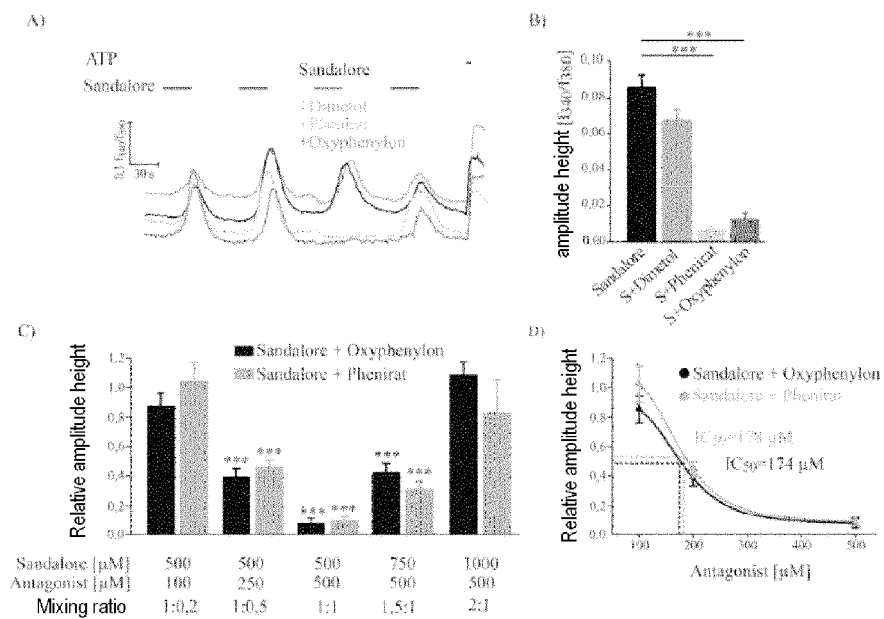

In order to characterize the antagonists, HaCaT cells were first repeatedly stimulated with Sandalore® (1 mM). On the third application, costimulation (1:1) with Sandalore® and one of the antagonists took place. On coapplication of Phenirat or Oxyphenylon, a significant reduction in Sandalore-induced calcium signals was recognizable, while in coapplication with dimetol, the calcium signals were only slightly reduced (FIGS. 15a and 15b). Based on this, dose-dependent characterization of inhibition was to be carried out. For this purpose, Sandalore® and the antagonists were costimulated with different concentrations. In combined application of Sandalore® (500 μM) with Oxyphenylon (500 μM) or Phenirat (500 μM), the calcium signals were significantly reduced to 8% or 9% of the control amplitude (Sandalore® without antagonists). On reduction of the antagonist concentration to 250 μM, inhibition of the Sandalore®-induced calcium signals and the amplitude heights was 39% or 45% of the control amplitudes. On further reduction of the antagonist concentration to 100 μM, the inhibitory action of the two antagonists disappeared completely (FIG. 15c). The $IC_{50}$ values (mean inhibitory concentrations) determined were 178 μM for Phenirat and 174 μM for Oxyphenylon (FIG. 15d).

With a constant antagonist concentration (500 μM) and a simultaneous increase in the Sandalore® concentration (750 μM), blocking by the antagonists also decreased. On a further increase to 1 mM of Sandalore®, inhibition by the antagonists was completely eliminated (FIG. 15c). Overall dose-dependent inhibition of Sandalore®-induced calcium signals by the antagonists Oxyphenylon and Phenirat was seen. This supports the results of the siRNA experiments and confirms the activation of OR2AT4 by the ligand Sandalore® in HaCaT cells.

Physiological Function of OR2AT4 in Human Keratinocytes

In calcium imaging experiments, changes in intracellular calcium concentration were induced in skin cells by short-term simulations (20 s) with Sandalore®. In regular use of creams or perfumes, however, odorants remain on the skin for longer periods (hours to days). Physiological effects that Sandalore® can trigger in such cases by activation of OR2AT4 in skin cells were investigated by means of long-term stimulation experiments.

Effect of Sandalore® Stimulation on Proliferation and Migration

Figure 16:
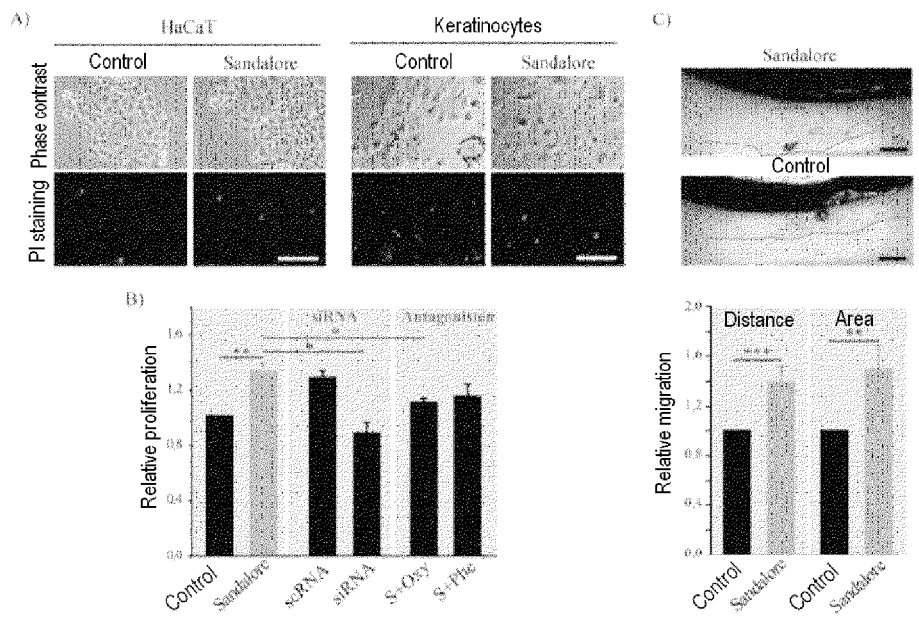

In order to obtain initial data on possible physiological effects caused by the activation of OR2AT4, HaCaT cells and primary keratinocytes were stimulated for five days with Sandalore®. By this method, potentially occurring apoptotic or necrotic effects were revealed by observing the morphology of the cells using a transmitted light microscope and subsequent propidium iodide (PI) staining, in which only the perforated membrane of necrotic or apoptotic cells is passed. After 5-day incubation with 500 µM of Sandalore®, neither the HaCaT cells nor the keratinocytes showed morphological changes or PI staining. A lethal effect of the odorant can therefore be ruled out (FIG. 16a).

It was next investigated whether Sandalore® has an effect on the growth behavior of skin cells. For this purpose, HaCaT cells were again stimulated for five days with Sandalore®, and cell count determination was carried out by means of a proliferation assay. It was found that Sandalore® increased the proliferation of the HaCaT cells compared to the control (0.1% DMSO) by 33% (FIG. 16b). In order to verify that this increase in proliferation is induced via activation of OR2AT4, HaCaT cells were transfected with siRNA or scRNA respectively, and the proliferation assay was repeated. HaCaT cells transfected with scRNA showed the same increase in proliferation as untransfected cells. However, transfection of siRNA caused a significant reduction in the effect induced by Sandalore® (FIG. 16b).

In addition, the cell count was determined after costimulation (1:1) by Sandalore® (500 µM) with the antagonists Oxyphenylon (500 µM) or Phenirat (500 µM). In the presence of the respective antagonists, proliferation was reduced. The effect was significant for Oxyphenylon. Oxyphenylon and Phenirat alone had no significant effect on the proliferation of the HaCaT cells.

Overall, the results of the siRNA and antagonist experiments showed that the growth-promoting action of Sandalore® is mediated by activation of OR2AT4. For example, slightly increased proliferation of keratinocytes takes place in reepithelialization processes. In addition to proliferation, migration of the skin cells is slightly increased in the process. For this reason, an agarose migration assay was conducted in order to determine whether the increased cell growth is accompanied by increased chemotactic behavior. In this assay, HaCaT cells were inoculated onto an agarose medium mixture, and propagation of the cells in the direction of 500 µM of Sandalore® or 0.1% DMSO was observed for five days. Measurement of the path traversed by the cells, or the area overgrown by the cells, showed significant chemotactic migration of the HaCaT cells in the direction of Sandalore® (FIG. 16c).

In summary, the results showed that via OR2AT4, Sandalore® induces a signal cascade that leads to an increase in the proliferation and migration of the HaCaT cells.

Effect of Sandalore® Stimulation on the Phosphorylation of MAP Kinases

Mitogen activated protein (MAP) kinases play an important roll in the transmission and conversion of extracellular stimuli into intracellular signals, thus regulating numerous processes such as cell differentiation, proliferation, and stress. The signalling pathways comprise at least three kinases successively activated by phosphorylation: an upstream MAP kinase kinase kinase (MAPKKK), a downstream MAP kinase kinase (MAPKK), and a terminal MAP kinase (MAPK). The MAPK signalling pathways are designated by their terminal MAPK, with the three most important being ERK1/2 (extracellular signal-regulated kinase) MAPK, p38 MAPK, and the JNK/SAPK (c-Jun NH2 terminal kinase/stress-activated phosphokinases).

Figure 17:
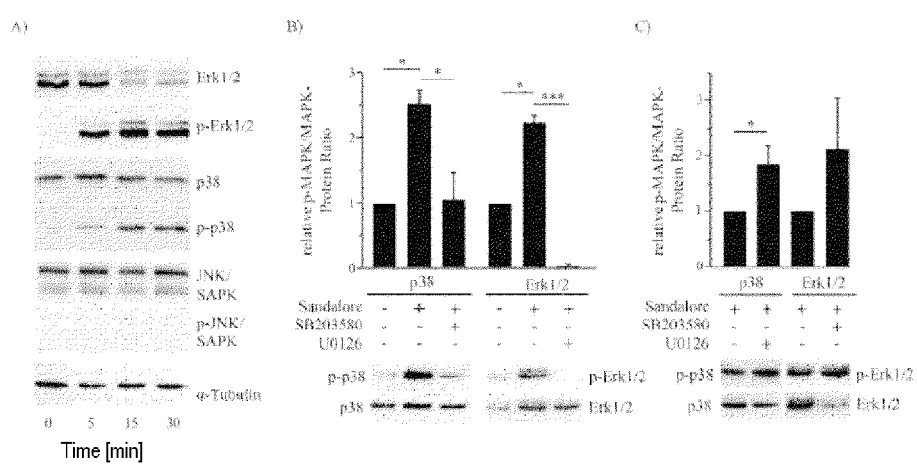

In the following, an investigation was to be conducted to determine whether a MAPK signalling pathway is activated by Sandalore® stimulation in skin cells, and if so, which pathway is involved. For detection, HaCaT cells were stimulated for 0-30 min with 500 µM of Sandalore®, and the proteins were then isolated and used in Western Blot assays. The results of the Western Blot showed increased phosphorylation of ERK1/2 MAPK and p38 MAPK within 5-30 min, but no phosphorylation of JNK/SAPK induced by cellular stress (FIG. 17a). Quantification of the Western Blot assay of the HaCaT cells showed a significant increase in the phosphorylation of ERK1/2 MAPK and p38 MAPK in 30-minute Sandalore® stimulation. In further incubation of the MAPK inhibitors SB203580 for p38 MAPK and U0126 for ERK1/2 MAPK, phosphorylation was again significantly reduced (FIG. 17b).

In order to reveal a possible interaction of the two MAPK signalling pathways, ERK1/2 phosphorylation in the presence of the p38 MAPK inhibitor SB203580 and p38 MAPK phosphorylation in the presence of the ERK1/2 MAPK inhibitor U0126 were investigated. Phosphorylation was increased for both kinases in the presence of the respective inhibitors compared to the cells stimulated with Sandalore® only. This effect was significant for p38 MAPK (FIG. 17c).

In summary, the results showed that p38 and ERK1/2 MAPK are phosphorylated by Sandalore® stimulation, and there is mutual regulation of the signalling pathways.

Figure 18:
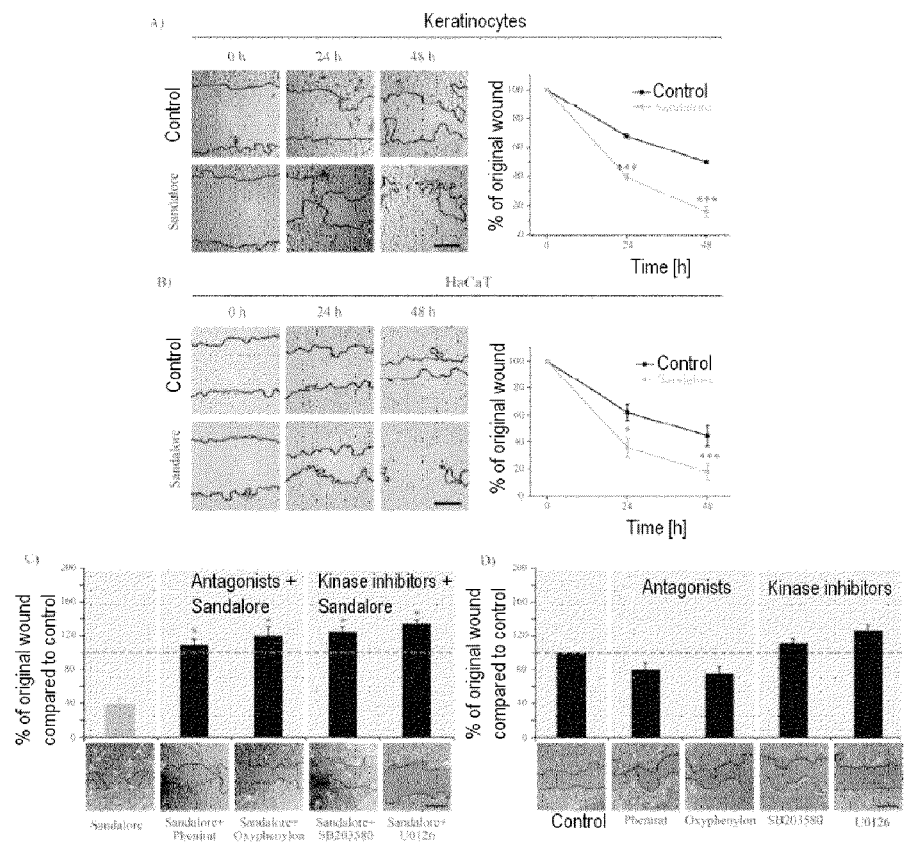

Effect of Sandalore® Stimulation on Human Keratinocytes in an In Vitro Wound Healing Assay The MAP kinases p38 and ERK1/2 are often associated with increased proliferation and migration in epidermal wound healing. For this reason, in a further physiological experiment, the effect of Sandalore® on "wound healing" of a confluent cell layer of HaCaT cells or primary keratinocytes was investigated. For this purpose, the wound scratch assay was used, which is an established in vitro method for initial investigations of wound healing processes in keratinocytes. In the wound scratch assay, a scratch was made in a confluent cell layer of HaCaT cells or primary keratinocytes using a pipet tip, and this "wound" was observed for two days. The results showed that this scratch closed 26% faster in the HaCaT cells and 34% in the keratinocytes when the cells were treated with 500 µM of Sandalore® (FIGS. 18a and 18b).

In order to investigate the role of the OR2AT4 receptor in this effect, a test was conducted to determine whether the two antagonists Oxyphenylon and Phenirat could again reduce the "wound healing" increased by Sandalore®. For this purpose, Sandalore® was mixed with one of the antagonists each in the same ratio, and the effect on "wound healing" of the HaCaT cells was again observed for 48 hours. It was found that coincubation again reduced "wound healing" to the normal level (FIG. 18c). The two antagonists alone had no effect on the "wound healing" (FIG. 18d). The role of the MAP kinases p38 and ERK1/2 was investigated by means of specific inhibitors of the kinases. For p38 MAPK, the ERK1/2 inhibitor SB203580 was used, and for ERK1/2 MAPK, the p38 inhibitor U0126 was used. In the presence of the respective inhibitors, the "wound healing" was also again reduced to the normal level (FIG. 18c), which confirms the role of p38 MAPK and ERK1/2 MAPK on Sandalore®-induced "wound healing" processes. The two inhibitors alone had no effect on the wound healing (FIG. 18d).

Investigation of Secretion of Interleukins and Phosphorylation of Akt Protein Kinase As shown above, Sandalore® has a positive effect on the "wound healing" of the cultivated keratinocytes in an in vitro wound assay. Wound healing is a complex process involving various physiological mechanisms. In order to obtain further information on how the OR2AT4-activated signal cascade contributes toward improved wound healing of skin cells, the production and secretion of interleukins after Sandalore® stimulation should be investigated by means of quantitative real-time PCR and an ELISA assay in HaCaT cells. Moreover, it should be verified by Western Blot analysis whether the protein kinase Akt, which is involved in differentiation processes in keratinocytes, is phosphorylated by Sandalore® stimulation.

Figure 19:
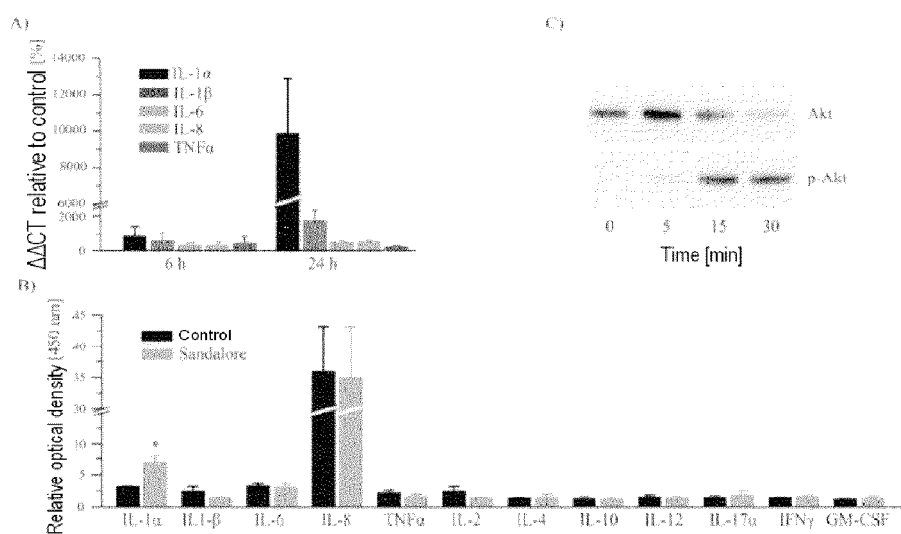

In order to investigate interleukin secretion, quantitative real-time PCR was first carried out. For this purpose, RNA from HaCaT cells was used that had previously been stimulated for 6 or 24 hours with Sandalore®. Detection was carried out with specific primers of various interleukins (IL-1α, IL-1β, IL-6, IL-8) and tumor necrosis factor (TNF■). It was found that after 24 hours, expression of IL-1α was increased by approx. 10,000% and that of interleukin IL-1β by approx. 1700% relative to the control (0.1% DMSO). For the other interleukins, there was no increase in the expression rate (FIG. 19a). In order to corroborate the results, an ELISA assay was carried out, in which the secreted interleukins in the supernatant of the cells can be detected by means of an immunological reaction. By means of the assay used, secretion of the interleukins (IL-1α, IL-1β, IL-2, IL-4, IL-6, IL-8, IL-10, IL-12, and IL-17α), TNFα, γ-interferon (IFNγ), and granulocyte macrophage colony-stimulating factor (GMCSF) was investigated. After 24-hour stimulation with Sandalore®, significantly increased secretion relative to the control (0.1% DMSO) was visible only for IL-1α. HaCaT cells showed extremely high secretion of IL-8, but this was not significantly higher than the control (0.1% DMSO) (FIG. 19b).

In addition to the phosphorylated kinases already detected, the phosphorylation of protein kinase Akt was investigated. For this purpose, HaCaT cells were stimulated with Sandalore® for 0, 5, 15 and 30 min, and phosphorylation was investigated by means of Western Blot assays and special antibodies to the unphosphorylated or phosphorylated form of the Akt-protein. It was found that the Akt kinase was phosphorylated within 5 min by Sandalore® stimulation, with this effect increasing further in longer-term stimulation (15 or 30 min) (FIG. 19c).

In summary, the results established that the expression and secretion of IL-1α was increased by Sandalore®, and that the protein kinase Akt, which is involved in differentiation processes of human keratinocytes, was activated.

EXPLANATION OF THE FOLLOWING FIGURES

In the following, the present invention is illustrated in greater detail by means of a number of figures, the content of which is discussed below.

FIG. 1

Heterologous expression of OR2AT4 in Hana3A cells. The Hana3A cells transiently transfected with OR2AT4 (top row) showed clear superposition in immunocytochemical staining with α-Rho antibody (red) and α-OR2AT4 antibody (green). In control staining of Hana3A cells transiently transfected with OR1A2s (bottom row), in contrast, only rhodopsin staining was identifiable. In order to determine the position and number of the cells, nuclear staining (DAPI, blue) was carried out in parallel. The fluorescence images were taken with a confocal microscope. Scale: 20 μm.

FIG. 2

Membrane expression of OR2AT4 in Hana3A cells. FIG. 2a shows live cell staining of Hana3A cells with α-Rho antibody. Left: Hana3A cells transiently transfected with OR2AT4 showed membrane staining. Right: Untransfected Hana3A cells showed no rhodopsin staining. The fluorescence images were taken with a confocal microscope. Scale: 20 μm. FIG. 2b shows quantification of the live cell staining. In order to determine the transfection rate, the total cell count (total) and number of transfected (transf.) cells were counted under a fluorescence microscope. Shown are the mean cell counts of three independent transfections including standard error.

FIG. 3

Determination of receptive field of recombinantly expressed OR2AT4. FIG. 3a shows the representative calcium imaging traces of transient OR2AT4-expressing Hana3A cells stimulated twice (20 s each, horizontal bars) with Sandalore® (1 mM). As a control, untransfected Hana3A cells were simulated with Sandalore®. 100 μM of ATP was used at the end of each measurement as a positive control stimulus. FIG. 3b shows evaluation of the calcium imaging measurements, in which transient OR2AT4-expressing Hana3A cells were stimulated with various sandalwood odorants (1 mM). The mean response rate including standard error of the cells is shown relative to the Ringer control. Number of measurements: Ringer (23), Sandalore® (22), Brahmanol® (14), Javanol (15), Sandranol (18), Polysantol (14), isobornyl cyclohexanol (14), sandalwood oil (14). Isobornyl.: isobornyl cyclohexanol; S. öl: sandalwood oil. Kruskal-Wallis test with multiple comparison. *: $p<0.05$. FIG. 3c shows evaluation of the dual luciferase assay. Significance was determined between Hana3A cells transfected with OR2AT4-pcDNA3 and pcDNA3 without an insert. The dots show mean normalized luciferase-activity including standard error. Mann-Whitney U test; n=3 experiments. *: $p<0.05$; : $p<0.01$; *: $p<0.001$.

FIG. 4

Figure 4:
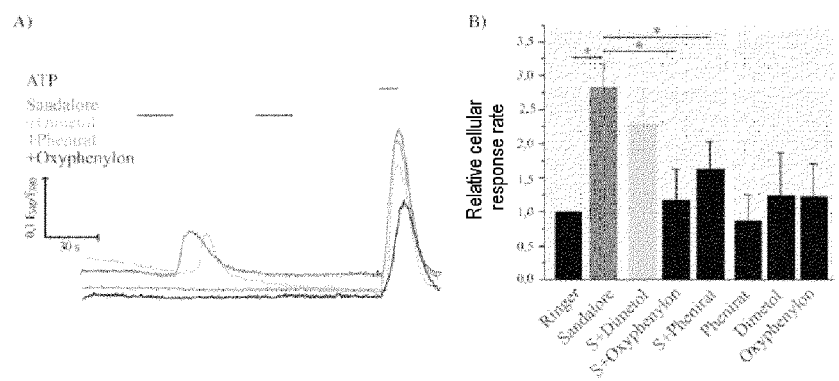

Antagonists of recombinantly expressed OR2AT4. The figure shows representative calcium imaging traces of transient OR2AT4-transfected Hana3A cells stimulated twice (20 s each, horizontal bars) with Sandalore® (blue traces), Sandalore®+dimetol (light blue traces), Sandalore®+Phenirat (gray traces), or Sandalore®+Oxyphenylon (black traces). 100 μM of ATP was used at the end of each measurement as a positive control stimulus. FIG. 4b shows evaluation of the calcium imaging measurements, in which transient OR2AT4-expressing Hana3A cells were simulated with various odorants (1 mM). The mean response rate including standard error of the cells is shown relative to the Ringer control. Number of measurements: Ringer (23), Sandalore® (22), Sandalore®+dimetol (11), dimetol (11), Phenirat (14), Sandalore®+Phenirat (22), Oxyphenylon (12), and Sandalore®+Oxyphenylon (20). S: Sandalore®. Kruskal-Wallis test with multiple comparison. *: p<0.05.

FIG. 5

Receptive field of OR2AT4 and structural formulae of odorants. The receptive field comprises the agonists (inner circle), the inactive substances (gray circle), and the antagonists (rectangle at upper right). For the sandalwood oil tested, the two principal components α-Santalol and β-Santalol are shown by way of example.

FIG. 6

Expression of OR2AT4 in various human skin cell types and tissues. In order to detect OR2AT4, PCR analysis was conducted with cDNA of various human RNA samples ("+"). Contamination with genomic DNA was ruled out based on a -RT sample ("-"). Fragment sizes: OR2AT4 (400 bp), β-actin (250 bp). M: marker, P: cell culture passage.

FIG. 7

Expression of OR2AT4 in HaCaT cells and human primary keratinocytes at the protein level. FIG. 7a shows HaCaT cells and primary keratinocytes, which showed clear immunocytochemical staining on use of an sα-OR2AT4 antibody (red). FIG. 7b shows that in control stains with a blocking peptide (block. peptide, ratio of OR2AT4 antibody to blocking peptide=1:2), staining was sharply reduced. In order to determine the position and number of the cells, nuclear staining (DAPI, blue) was carried out in parallel. The fluorescence images were taken with a confocal microscope. Scale: 20 μm.

FIG. 8

Expression of OR2AT4 in human skin sections. As seen in FIG. 8a, the epidermal keratinocytes showed clear immunocytochemical staining with α-OR2AT4 antibody (green). FIG. 8b shows the control stains, in which the primary antibody was replaced with rabbit serum; in this case, staining was sharply reduced. Top: 400× magnification; bottom: sectional view. E: epidermis, D: dermis, B: basal layer.

FIG. 9

Effect of the OR2AT4 ligand Sandalore® on intracellular calcium concentration of cultivated keratinocytes. In both A) primary keratinocytes (n=175 cells) and B) HaCaT cells (n=186 cells), Sandalore® (500 μM) induced calcium signals in calcium imaging experiments with repeated stimulation (horizontal bars). Left: Representative calcium imaging trace of the Sandalore-induced calcium signals. 100 μM of ATP was used at the end of each measurement as a positive control stimulus. Right: Quantitative evaluation of calcium signals in 4-time application of Sandalore® (500 μM). Shown are the mean values of the individual applications including standard error. Mann-Whitney U test. *: p<0.05. C) and D): dose-dependent activation of HaCaT cells in calcium imaging experiments. Shown are the mean amplitudes including standard error at various concentrations in the first (C) and fourth (D) Sandalore® application. Number of cells measured: 0.0125 mM (39), 0.025 mM (30), 0.1 mM (46), 0.5 mM (34), 1 mM (63), 2 mM (41), 10 mM (36).

FIG. 10

Effect of gap junction blockers on sensitization of Sandalore®-induced calcium signals. A) Representative calcium imaging traces of HaCaT cells (left) and primary keratinocytes (right) incubated with the gap junction blocker 1-octanol (500 μM) and then repeatedly stimulated with Sandalore® (500 μM, horizontal bars) (blue trace). The black trace shows repetitive Sandalore® stimulation without pre-incubation with the blocker (control). 100 μM of ATP was used at the end of each measurement as a positive control stimulus. Quantitative evaluation of HaCaT cells (B) and primary keratinocytes (C) incubated with the gap junction blockers 1-octanol (500 μM) or carbenoxolone (10 μM) and then repeatedly stimulated with Sandalore® (500 μM) or Lyral (1 mM) in calcium imaging experiments. Shown are the mean values of the individual applications including standard error relative to the control measurements (Sandalore® application without blocker). Mann-Whitney U test. Number of cells measured: Sandalore®+1-octanol (HaCaT (110), keratinocytes (26)); Sandalore®+carbenoxolone: HaCaT (74); Lyral+carbenoxolone: HaCaT (43). ***: p<0.001.

FIG. 11

Pharmacological characterization of Sandalore®-induced signal cascade in human keratinocytes. A)-D). Shown are representative calcium imaging traces of primary keratinocytes in the presence of a blocker (blue). The horizontal bars correspond to the application times. 100 μM of ATP was used at the end of each measurement as a positive control stimulus. A) Measurement with calcium-free extracellular solution (+10 mM EGTA). B) Measurement with the adenylyl cyclase blocker SQ-22536 (100 μM). C) Use of the phospholipase-C blocker U-73122 (10 μM). 100 μM of histamine was taken as a positive control. D) Measurement with the CNG channel blocker L-cis-diltiazem (150 μM). E) Overview of pharmacological measurement of HaCaT cells and primary keratinocytes (Kera). The mean amplitudes relative to the control measurements (dashed line) are indicated. MDL-12330A (40 μM). EGTA: calcium-free Ringer (HaCaT n=46, Kera n=52), SQ: SQ-22536 (HaCaT n=60, Kera n=26), MDL: MDL-12330A (HaCaT n=69, Kera n=24), U-73122 (HaCaT n=41, Kera n=25), L-cis-D.: L-cis-diltiazem (HaCaT n=41, Kera n=25). Mann-Whitney U test. ***: p<0.001. F) Determination of the cAMP contents of HaCaT cells after stimulation with Sandalore® by means of cAMP-Glo™ assays. The dots show the mean cAMP content including standard error after 10-minute Sandalore® stimulation (1 μM-10,000 μM). Significance was determined between HaCaT cells stimulated with Sandalore® and stimulated with an equivalent volume of DMSO (0.2%). Kruskal-Wallis Test with multiple comparison; n=3 experiments. *: p<0.05.

FIG. 12

Expression analysis of signal cascade components and structurally related proteins by means of NGS data and RT-PCR. A) Overview of NGS results and RT-PCR. The results of the NGS data are given as FPKM values. Successful detection of the transcripts in RT-PCR experiments is indicated by (✓); no detection is indicated by (x). n.d.: no data. Components of the olfactory signal cascade indicated by (*). B) RT-PCR of various signal cascade components. Fragment sizes: AC3 (311 bp), ANO1 (288 bp), ANO6 (432 bp), ANO8 (427 bp), ANO9 (416 bp), ANO10 (373 bp), CNGA1 (2790 bp), CNGB1 (288 bp), GNAL (485 bp). M: marker, K: control, GNAL: GαolfR subunit, GNAS: G■SR subunit, ADCY: adenylyl cyclase, ANO: anoctamin (transmembrane protein 16).

FIG. 13

Expression analyses of AC3 and CNGA1 by means of immunocytochemical stains. A) HaCaT cells and primary keratinocytes showed clear immunocytochemical staining with the specific antibodies α-Gαolf, α-CNGA1 and α-AC3. Stains in which only the second antibody was used were taken as a control. In order to determine the position and number of the cells, nuclear staining (DAPI, blue) was carried out in parallel. The fluorescence images were taken with a confocal microscope. Scale: 20 μm. B) Detection of AC3 expression in human skin sections by means of immunocytochemical staining. Epidermal keratinocytes showed clear immunocytochemical staining when α-AC3 antibody (green) was used. In control stains, in which the primary antibody was replaced with rabbit serum, no specific staining was visible. 400× magnification. E: epidermis, D: dermis, B: basal layer.

FIG. 14

RNA interference experiments for verifying the role of OR2AT4 in Sandalore-induced calcium signals in HaCaT cells. A) Dual luciferase assay for determination of siRNA activity in Hana3A cells. Shown is the normalized luminescence signal (firefly/*Renilla*) of Hana3A cells cotransfected with siRNA or scRNA and the reporter vector pmirGLO-OR2AT4 compared to cells transfected only with pmirGLO-OR2AT4. Mann-Whitney U test, n=3 experiments. *: p<0.001. B) Left: immunocytochemical stains of HaCaT cells transfected with siRNA or scRNA-expressing plasmids and α-OR2AT4 antibody (red). siRNA or scRNA-expressing cells can be identified based on GFP expression (green). Right: Quantitative evaluation showed a significant reduction in α-OR2AT4 staining of the siRNA-expressing cells (n=17 cells) compared to the scRNA-expressing cells (n=17 cells). Shown are the mean fluorescence intensities including standard error of the siRNA relative to the scRNA-expressing cells. Mann-Whitney U test. : p<0.01. C) Transmitted light and fluorescence image of HaCaT cells transfected with a mixture of the two siRNAs. Scale: 50 μm. D) Fluorescence images of calcium imaging measurement. The siRNA-expressing cell (circle) was identified by coexpression of GFP and showed no increase in intracellular calcium concentration on stimulation with Sandalore. E) Representative calcium imaging trace of HaCaT cells transfected with siRNA (blue trace) or scRNA (black trace) that were repeatedly stimulated with Sandalore® (500 μM, horizontal bars). 100 μM of ATP was used at the end of the measurement as a control stimulus. F) Quantitative evaluation of Sandalore-induced calcium signals in siRNA and scRNA-expressing cells. The amplitudes of the calcium signals were first standardized to ATP, and the siRNA-expressing cells were then expressed relative to the scRNA-expressing HaCaT cells. Shown are the mean values of the individual applications including standard error. Mann-Whitney U Test; n=18 cells (siRNA), n=17 cells (scRNA). *: p<0.05; **: p<0.01.

FIG. 15

Action of antagonists of OR2AT4 on Sandalore®-induced calcium signals in HaCaT cells. A) Representative calcium imaging traces of HaCaT cells repeatedly stimulated with Sandalore® (1 mM). In the third application, stimulation with Sandalore® (dark blue trace) or costimulation with Sandalore®+dimetol (light blue trace), Sandalore®+Oxyphenylon (black trace), or Sandalore®+Phenirat (gray trace) was carried out. 100 μM of ATP was used at the end of each measurement as a control stimulus. The horizontal bars correspond to the application times. Odorants: 1 mM. B) Quantitative evaluation of the calcium signals on stimulation with Sandalore® alone or costimulation with Dimetol, Phenirat, or Oxyphenylon. S.: Sandalore®. Shown are the mean values of the third application including standard error. Mann-Whitney U test. *: p<0.001. Number of cells measured: Sandalore® (121), Sandalore®+Oxyphenylon (43), Sandalore®+Phenirat (67), Sandalore®+dimetol (120). C) Investigation of dose-dependent inhibition of Sandalore®-induced calcium signals by the antagonists Oxyphenylon and Phenirat. HaCaT cells were costimulated in the third application with various concentrations of Sandalore® (500-1000 μM) and one antagonist each (100-500 μM). For comparability of the odorant-induced calcium signals, the amplitudes of the third application were standardized to the preceding application. Shown are the mean values including standard error of the standardized odorant-induced calcium signals relative to the control cells (Sandalore® application without antagonists). Mann-Whitney U test. *: p<0.001. D) Calculation of the IC50 values for the antagonists from the data for 500 μM given under C).

FIG. 16

Effect of Sandalore® long-term stimulation on morphology, growth, and migration processes in keratinocytes. A) Phase contrast image and PI stains of HaCaT cells and primary keratinocytes after stimulation with Sandalore® (500 μM) or 0.1% DMSO (control) for five days. On positive PI staining, the cell nuclei are stained red. Scale: 100 μm. B) Evaluation of the proliferation assay carried out with the CyQuant Cell Proliferation Kit on HaCaT cells after 5-day stimulation with 500 μM of Sandalore® or 0.1% DMSO (control). For the RNA interference experiments, the cells were transfected with siRNA or scRNA on the day before Sandalore® stimulation. Shown is the mean cell count including standard error relative to untreated cells. Mann-Whitney U test; n=3 experiments. *: p<0.05; : p<0.01. S: Sandalore. C) Agarose assay for determination of migration of HaCaT cells. Top: Transmitted light images of HaCaT cells that have migrated in the direction of Sandalore® (500 μM) or 0.1% DMSO. The growth margin of the cells was surrounded in black. Scale: 250 μm. Bottom: Evaluation of the proliferation assay. The longest path traversed by the cells and the overgrown area were measured and compared to the control (0.1% DMSO). Paired two-sided T test. Mean values including standard error; n=4 experiments. : p<0.01; ***: p<0.001.

FIG. 17

Effect of Sandalore® stimulation on phosphorylation of MAP kinases in skin cells. A) Western Blot for investigating the phosphorylation of the MAP kinases in HaCaT cells stimulated for 0, 5, 15 and 30 min with Sandalore®(500 μM). In order to confirm uniform protein volume, ■-tubulin was used as a control. ERK1/2: 42/44 kDa; p38: 43 kDa; JNK/SAPK: 46/54 kDa; ■-tubulin: 52 kDa. B) Quantitative evaluation of p38 and ERK1/2 phosphorylation of HaCaT cells stimulated for 30 min with Sandalore®(500 μM) or additionally with the p38 inhibitor SB203580 (10 μM) or ERK1/2 inhibitor U0126 (10 μM). For evaluation, the ratio of the phosphorylated (p) and unphosphorylated proteins was established and compared to that of untreated cells. Mean values including standard error. Mann-Whitney U test. *: p<0.05; ***: p<0.001. In C), the inhibitors of the respective other MAP kinase were used, and phosphorylation was compared to the cells stimulated with Sandalore® (500 μM) alone. Mean values including standard error. Mann-Whitney U test. *: p<0.05. The Western Blot analyses were carried out with three different protein isolations.

FIG. 18

Effect of Sandalore® stimulation on human keratinocytes in an in vitro "wound healing" assay. Investigation of the "wound healing rate" of A) primary keratinocytes and B) HaCaT cells by means of a wound scratch assay in the presence of Sandalore® (500 μM) or 0.1% DMSO as a control. Left: Transmitted light images of the "wound" observed at various times. The growth margin of the cells was surrounded in black. Scale: 200 μm. Right: Quantitative evaluation of the wound scratch assay. The areas of the wounds were measured and compared to the initial wound (0 h). Mean values including standard error. Mann-Whitney U test; n=4 experiments. *: p<0.05; ***: p<0.001. C) Wound scratch assay in the presence of Sandalore® (500 μM) and one of the antagonists Oxyphenylon (500 μM) or Phenirat (500 μM) respectively, the p38 MAPK inhibitor SB203580 (10 μM), or the ERK1/2 MAPK inhibitor U0126 (10 μM). The measured wound areas of the treated cells (after 48-hour stimulation) were compared to the control (0.1% DMSO). Mean values including standard error. Kruskal-Wallis test with multiple comparison; n=3 experiments. *: p<0.05. D)

Controls for the wound scratch assay with Oxyphenylon (500 µM), Phenirat (500 µM), 5B203580 (10 µM), or U0126 (10 µM) carried out under C). The measured wound areas of the treated cells were compared to the control (0.1% DMSO). Mean value included.

FIG. 19

Investigation of interleukin secretion and phosphorylation of Akt protein kinase after Sandalore® stimulation. A) Investigation of the regulation of interleukins in HaCaT cells by means of qRT-PCR after stimulation with Sandalore® (500 µM) for 6 h and 24 h. 0.1% DMSO was used as a control. GAPDH was used as a reference gene, and the relative expression between untreated and stimulated cells was determined. Mean values including standard error. n=3 experiments. B) ELISA assay for the detection of interleukins in the supernatant of HaCaT cells stimulated for 24 h with Sandalore® (500 µM). 0.1% DMSO was used as a control. The measured optical density of the treated cells at 450 nm was expressed relative to the background. Supernatants of three independent stimulations were used. Mean values including standard error. Mann-Whitney U test. *: p<0.05. C) Western Blot for investigating phosphorylation of Akt protein kinase by HaCaT cells stimulated for 0, 5, 15, and 30 min with Sandalore® (500 µM). Akt (60 kDA); p-Akt: phosphorylated Akt protein (60 kDA).

The invention claimed is:

1. A method for acceleration of wound healing, by applying a cell regenerating effective amount of a drug consisting essentially of a derivative of the formula (I)

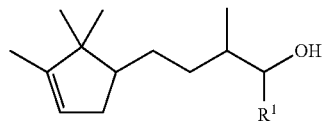

(I)

in which $R^1$ denotes methyl, to activate the olfactory receptor OR2AT4.

2. The method for acceleration of wound healing of claim 1, comprising using an effective amount of the drug according to claim 1 to stimulate the proliferation and migration of cells.

3. The method for acceleration of wound healing of claim 1, comprising using an effective amount of the drug according to claim 1 to stimulate the phosphorylation of MAP kinases.

4. The method for acceleration of wound healing of claim 1, comprising using an effective amount of the drug according to claim 1 to stimulate the expression and secretion of interleukin IL-1α.

5. A method for acceleration of healing a wound that results from the opening of tissue from the epidermis, resulting in a need for tissue closure via tissue regeneration by applying to the wound that results from the opening of tissue, a cell regenerating effective amount of a drug consisting essentially of a derivative of formula (I)

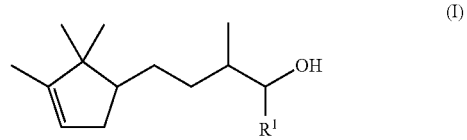

(I)

in which $R^1$ denotes hydrogen or methyl, effective to accelerate tissue regeneration at the wound site, and wherein the drug activates the olafactory receptor OR2AT4, increases the proliferation and migration of HaCaT cells and regenerates cells at the wound site at a rate increased by the application of the drug to the wound.

6. The method of claim 5, wherein $R^1$ is methyl.

7. The method of claim 5, wherein $R^1$ is H.

* * * * *